US012274826B2

(12) United States Patent
Adametz

(10) Patent No.: US 12,274,826 B2
(45) Date of Patent: Apr. 15, 2025

(54) ALTERATION-FREE GAS CONTROL DEVICE FOR A VENTILATOR

(71) Applicant: Loewenstein Medical Technology S.A., Luxembourg (LU)

(72) Inventor: Benjamin Adametz, Hamburg (DE)

(73) Assignee: LOEWENSTEIN MEDICAL TECHNOLOGY S.A., Luxembourg (LU)

( * ) Notice: Subject to any disclaimer, the term of this patent is extended or adjusted under 35 U.S.C. 154(b) by 1137 days.

(21) Appl. No.: 17/257,915

(22) PCT Filed: Jul. 5, 2019

(86) PCT No.: PCT/DE2019/000185
§ 371 (c)(1),
(2) Date: Jan. 5, 2021

(87) PCT Pub. No.: WO2020/007388
PCT Pub. Date: Jan. 9, 2020

(65) Prior Publication Data
US 2021/0275762 A1 Sep. 9, 2021

(30) Foreign Application Priority Data
Jul. 6, 2018 (DE) .......................... 102018005340.8

(51) Int. Cl.
*A61M 16/00* (2006.01)
*A61M 16/20* (2006.01)

(52) U.S. Cl.
CPC ...... *A61M 16/022* (2017.08); *A61M 16/0003* (2014.02); *A61M 16/205* (2014.02); *A61M 2016/0027* (2013.01); *A61M 2016/0039* (2013.01); *A61M 2016/0042* (2013.01); *A61M 16/0066* (2013.01); *A61M 2205/3331* (2013.01)

(58) Field of Classification Search
CPC ............ A61M 16/201; A61M 16/0057; A61M 16/0883; A61M 16/022; A61M 16/208; A61M 2205/3334; A61M 16/00
See application file for complete search history.

(56) References Cited

U.S. PATENT DOCUMENTS

2003/0145855 A1* 8/2003 Fuhrman ............. A61M 16/206
128/204.22
2011/0197889 A1* 8/2011 Lahde ............... A61M 16/0833
128/205.12

FOREIGN PATENT DOCUMENTS

| CN | 105617527 A | 6/2016 |
| CN | 107308531 A | 11/2017 |
| DE | 102004063158 A1 | 7/2006 |
| GB | 1190441 A | 5/1970 |

* cited by examiner

*Primary Examiner* — Margaret M Luarca
(74) *Attorney, Agent, or Firm* — Abel Schillinger, LLP

(57) ABSTRACT

A ventilator for use with alternative hose systems. The ventilator comprises at least one respiratory gas source, at least one respiratory gas path, at least one appliance outlet, an appliance inlet and a gas control device for presetting the ventilator for use of the alternative hose systems by switching at least one switching mechanism The gas control device is configured for use of a hose system which is a leakage system, for opening the respiratory gas path (bypass) for a respiratory gas flow.

29 Claims, 14 Drawing Sheets

ALTERATION-FREE GAS CONTROL DEVICE FOR A VENTILATOR

BACKGROUND OF THE INVENTION

1. Field of the Invention

The present invention relates to a gas control device, wherein the gas control device is arranged in a ventilator which is designed to provide a gas supply to and gas removal from a patient, wherein the gas control device comprises a first gas duct with a nonreturn valve, a second gas duct and a switching mechanism, wherein the first gas duct has a gas discharge opening with a sealing membrane and a closure cap.

2. Discussion of Background Information

Ventilators are used for treating respiratory disorders; the ventilators can be used in non-invasive and invasive ventilation, both in and out of hospitals.

For ventilation of a patient, use can generally be made of a ventilator with an inspiratory branch for the inspiratory respiratory gas flow and optionally with a branch for the expiratory respiratory gas flow. The branch for the expiratory respiratory gas flow enables the exhalation/expiration of a respiratory gas by the patient, while the branch for the inspiratory respiratory gas flow supplies the patient with respiratory gas.

The ventilators can be connected in operation to a hose system with a passive exhalation opening/leakage hose system or to a hose system with an active exhalation valve/valve hose system.

It is possible, in the case of ventilators known in the prior art, to change between ventilation with a leakage hose system and a valve hose system. However, it has hitherto been necessary to alter/install one or more components, for example a nonreturn valve, outside or inside the appliance. A leakage hose system here is a single-hose system with a defined leakage opening through which respiratory gas can continuously escape during the ventilation in order to flush out carbon dioxide. A valve hose system is a single-hose system with a switching valve for the expiration, or a double-hose system, in which exhaled respiratory gas is supplied again to the ventilator for monitoring purposes. Ventilators therefore have at least two connecting ports for either the double-hose system or the single-hose system. In addition, ventilators have pressure ports which are necessary for use of single-hose systems with a valve, in order to conduct a control pressure to the valve. In the case of ventilators known in the prior art, an appropriate adapter therefore always has to be for the selected hose system and, in addition, pressure ports possibly have to be closed or opened. Before the patient hose system can be connected, the appropriate hose system adapter has to be installed. However, the installation/alteration is time-consuming, error-prone and is an obstacle to use.

It is therefore the object of the invention to provide a device which makes it possible to use a ventilator both together with a leakage hose system and together with a valve hose system without alteration measures or without adapters.

This object is achieved by a gas control device or a ventilator as claimed in claim 1. Developments and advantageous refinements are the subject matter of the dependent claims. Further advantages and features emerge from the general description and from the description of the exemplary embodiments.

The present invention relates to a ventilator for use with alternative hose systems, wherein the ventilator comprises at least one respiratory gas source, at least one respiratory gas path, at least one appliance outlet, and an appliance inlet, and a gas control device for presetting the ventilator for use of the alternative hose systems by switching at least one switching mechanism, wherein the gas control device is designed and configured for use of a hose system, which is a leakage system, for opening the respiratory gas path (bypass) for a respiratory gas flow.

The ventilator is also characterized in that gas control device is configured and designed to activate the switching mechanism to open the respiratory gas path (bypass) for a respiratory gas flow and to activate the switching mechanism to close the connection.

The ventilator is also characterized in that the gas control device is designed and configured not to conduct a control pressure to the patient valve and/or and not to activate/to use the flow sensor.

The ventilator is also characterized in that the gas control device is designed and configured for use of a hose system, which is a valve system with a patient valve, to block the respiratory gas path and to open the connection in order to switch a control pressure to the patient valve.

SUMMARY OF THE INVENTION

The ventilator is also characterized in that the gas control device is designed and configured for use of a valve system with a patient valve to activate the switching mechanism to block a respiratory gas flow through the respiratory gas path and to activate the switching mechanism to open the connection in order to switch a control pressure to the patient valve.

The ventilator is also characterized in that the gas control device is designed and configured not to conduct a control pressure to the patient valve and not to activate/to use the flow sensor.

The ventilator is also characterized in that gas control device is designed and configured for use of a hose system, which is a two-hose system, to block the respiratory gas path and to block the connection.

The ventilator is also characterized in that the gas control device is designed and configured to activate the switching mechanism to block a respiratory gas flow through the respiratory gas path and to activate the switching mechanism to block the connection.

The ventilator is also characterized in that the gas control device is designed and configured to conduct a control pressure to the patient valve and to activate the flow sensor.

The ventilator is also characterized in that the gas control device is designed and configured for use:
- of a leakage system to activate the switching mechanism to open the respiratory gas path (bypass) for a respiratory gas flow
- of a valve system with a patient valve to activate the switching mechanism to block a respiratory gas flow through the respiratory gas path, and activates the switching mechanism to open the connection in order to switch a control pressure to the patient valve
- of a two-hose system to activate the switching mechanism to block a respiratory gas flow through the respiratory gas path and to activate the switching mechanism to block the connection.

The ventilator is also characterized in that the gas control device is embodied pneumatically and/or electronically and, in accordance with a user specification, via a user interface, or automatically, if the hose systems because of technical identifiers are identified by an identification system of the ventilator, presets the ventilator for use of the alternative hose systems.

The gas control device comprises at least the nonreturn valve, the bypass and the valve.

The gas control device comprises all of the valves and switching mechanisms and respiratory gas sources.

The ventilator is also characterized in that the respiratory gas path and the appliance outlet and the connection and the at least one switching mechanism are designed and configured to be alteration-free and adapter-less such that a change of the hose systems is possible without adapters or without tools.

In particular, the appliance inlet and the appliance outlet remain alteration-free on the ventilator. For use of the different hose systems, adapters for the appliance inlet and the appliance outlet are unnecessary in the event of a change of said hose systems. In particular, appliance inlet or appliance outlet or the ports do not have to be closed with stoppers or caps.

The ventilator is also characterized in that the switching mechanism is embodied as a valve which at least temporarily switches the rebreathing pressure of the expiration of the patient as a control pressure to the valve.

The ventilator is also characterized in that the switching mechanism is embodied as a closure valve which switches the control pressure originating from the respiratory gas source to the pressure port when the latter is connected to the patient valve of the single-hose system.

The ventilator is also characterized in that the pressure sensor is switched to inactive when a leakage system is used, but can also remain active if the hose system has a pressure-measuring point.

The ventilator is also characterized in that the flow sensor is switched to inactive or is not used when a leakage system is used.

The ventilator is also characterized in that the flow sensor 32c is switched to inactive when a single-hose system is used.

The ventilator is also characterized in that the gas control device is designed to ensure the conducting of gas in a ventilator with an operatively connected leakage hose system and with an operatively connected valve hose system, wherein the gas control device is configured to be alteration-free in the ventilator in the event of a change between leakage hose system and valve hose system.

The ventilator is also characterized in that the ventilator comprises a respiratory gas path which extends between an appliance inlet and an appliance outlet, wherein the respiratory gas path comprises a respiratory gas drive and a gas control device with a nonreturn valve, a bypass and a switching mechanism a, wherein the respiratory gas drive conducts an inspiratory respiratory gas flow from the appliance inlet through the nonreturn valve to the appliance outlet, characterized in that the nonreturn valve is designed and arranged to prevent a respiratory gas flow in the direction of the appliance inlet (in the blocking direction of the nonreturn valve), and the bypass is configured and arranged to permit a respiratory gas flow for bypassing the nonreturn valve, and the switching mechanism a is configured and arranged to at least temporarily permit or to interrupt a respiratory gas flow through the bypass for bypassing the nonreturn valve.

The ventilator is also characterized in that the respiratory gas flow runs through the bypass counter to the blocking direction of the nonreturn valve.

The ventilator is also characterized in that the switching mechanism a is arranged in the bypass, and the bypass branches off from the respiratory gas path, upstream of the nonreturn valve, and opens again downstream of the nonreturn valve into the respiratory gas path or into the appliance inlet.

The ventilator is also characterized in that the respiratory gas drive is arranged between the appliance inlet and the nonreturn valve.

The ventilator is also characterized in that the respiratory gas drive is arranged between nonreturn valve and the appliance outlet.

The ventilator is also characterized in that the switching mechanism is arranged in the bypass, and the bypass branches off between the respiratory gas drive and the nonreturn valve and opens again between the nonreturn valve and the appliance outlet into the respiratory gas path, and wherein the respiratory gas drive is arranged between the appliance inlet and the nonreturn valve, and, via the switching mechanism arranged in the bypass, respiratory gas can be returned in the direction of the appliance inlet, as a result of which the nonreturn valve is bypassed.

The ventilator is also characterized in that the switching mechanism a is arranged in the bypass, and the bypass branches off between the appliance inlet and the nonreturn valve and opens again between the nonreturn valve and the respiratory gas drive into the respiratory gas path, wherein the respiratory gas drive is arranged between the nonreturn valve and the appliance outlet and, via the switching mechanism arranged in the bypass, respiratory gas can be returned in the direction of the appliance inlet after it has passed through the respiratory gas drive.

The ventilator is also characterized in that a second respiratory gas path leads from an appliance inlet to the appliance outlet, wherein the second respiratory gas path opens into the first respiratory gas path upstream of the appliance outlet and downstream of the nonreturn valve and downstream of the respiratory gas drive.

The ventilator is also characterized in that a nonreturn valve and/or a respiratory gas drive is arranged in the second respiratory gas path in order to conduct a defined respiratory gas flow from the appliance inlet to the appliance outlet.

The ventilator is also characterized in that a gas-measuring mechanism is arranged between the bypass and the appliance outlet and is configured to detect a flow or a volume or a pressure of the respiratory gas in the respiratory gas path, and the switching mechanism a is designed and configured to set a PEEP (positive end-expiratory pressure) in the range of 0-20 hPa, preferably 0-15 hPa.

The ventilator is also characterized in that the ventilator has an expiratory respiratory gas path which extends from an expiratory appliance inlet to an expiratory appliance outlet and comprises a switching mechanism and a gas-measuring mechanism, wherein the gas-measuring mechanism is arranged between the expiratory appliance outlet and the switching mechanism.

The ventilator is also characterized in that a hose system 33 is mounted on the appliance outlet, wherein the hose system 33 has a first branch 34 and a second branch 35, wherein the first branch 34 leads from the appliance outlet to a patient interface 36, and a second branch 35 leads from the patient interface 36 to the expiratory appliance inlet 38, wherein inspiratory respiratory gas is conducted from the inspiratory respiratory gas path to the patient interface 36 via the first branch 34, and expiratory respiratory gas is conducted from the patient interface 36 to the expiratory respiratory gas path via the second branch 35.

The ventilator is also characterized in that in the event of a blockage/disturbance of the expiratory respiratory gas path, the expiratory respiratory gas can be conducted away into the inspiratory respiratory gas path and via the open bypass into the surroundings by control of the switching mechanism.

The ventilator is also characterized in that the ventilator has a first inspiratory respiratory gas path and a second inspiratory respiratory gas path, and also an expiratory respiratory gas path and a separate expiratory respiratory gas path.

According to the invention, the gas control device is designed to ensure the conducting of gas in the case of a ventilator with an operatively connected leakage hose system and with an operatively connected valve hose system, wherein the gas control device is configured to be alteration-free in the ventilator in the event of a change between leakage hose system and valve hose system.

The gas control device according to the invention is thus designed both for use in a ventilator which is operatively connected to a leakage hose system and for use in a ventilator which is operatively connected to a valve hose system. The present invention is distinguished here in that the gas control device is alteration-free. Alteration-free means that a change can be made between the leakage hose system and the valve hose system on a ventilator without the gas control device in/on the ventilator having to be altered. This affords the advantage that the gas control device designed in such a manner can be used both in a ventilator which is operated in the leakage hose system and in a ventilator which is operated in the valve hose system.

In the event of a change from a leakage hose system/leakage system to a valve hose system/valve system, in the present gas control device gas has to be rerouted in the gas ducts in order, for example in the case of a leakage hose system, to remove respiratory gas/gas through the opening of the first gas duct such that a rise in pressure or a blockage of the gas flow in the interior of the hose system does not occur. The gas control device according to the invention is thus designed to reroute the gas in the ventilator when required, in such a manner that the gas can be conducted via different gas ducts of the ventilator.

In an alternative embodiment, a ventilator can comprise at least two gas control devices in order optimally to guide a gas flow in the ventilator depending on a selected hose system or on a blockage/disturbance that occurs.

In one refinement, the gas control device comprises a switching mechanism, wherein the switching mechanism is designed to switch between at least two switching modes which set up the ventilator for use of at least two different hose systems. The present gas control device comprises at least one switching mechanism. The switching modes are advantageously stored in the switching mechanism. The switching modes can generally be stored in the gas control device/switching mechanism, wherein the switching modes are advantageously configured to be adjustable. In an advantageous manner, the gas control device or switching mechanism is designed to be adjustable by means of a blocking function carried out only by technical personnel. Alternatively, preset switching modes are stored. The switching modes can be switched/changed according to an expiration of the ventilator or according to an inspiration. Alternatively, the switching modes can be changed manually or automatically.

In a further refinement, the switching mechanism is designed to switch the gas control device into a first switching mode when a leakage hose system is used and to switch same into a second switching mode when a valve hose system is used.

The first switching mode is generally distinguished in that the switching mechanism is switched in such a manner that, in the event of a change to a leakage hose system, the gas flow of the first gas duct can be continuously removed via the opening in the first gas duct. For this purpose, the switching mechanism is designed not to charge the gas flow of the second gas duct with a working pressure, when the first switching mode is set, and therefore a sealing membrane which rests on the opening can be lifted by the gas flow of the first gas duct and the gas/the gas flow of the first gas duct can escape via the opening. The first switching mode is advantageously permanently present when the gas control device is used in a leakage hose system. This guarantees a continuous outflow of gas at the opening, and therefore a rise in pressure or a blockage in the first gas duct of the ventilator does not occur.

The second switching mode is generally distinguished in that the switching mechanism is switched in such a manner that, in the event of a change to a valve hose system, the switching mechanism charges the gas flow of the second gas duct with a working pressure such that the charged gas flow of the second gas duct seals the sealing membrane on the opening, and therefore the gas flow of the first gas duct cannot escape via the opening. This affords the advantage that there is no rebreathing into the ventilator in the expiration, which would cause a deterioration in the removal of $CO_2$ of the respiratory gas. The second gas duct is therefore generally configured as a pressure duct.

In a development of the invention, the switching mechanism is designed to switch into a third switching mode in the event of a blockage of an expiratory branch of the ventilator. The third mode is designed here similarly to the first switching mode, wherein the gas flow of the first gas duct can escape via the opening. The third switching mode can be used, for example, if a respiratory gas drive/a blower fails. In this case, the third switching mode makes it possible for the patient to intake gas from the surroundings. The third switching mode is generally designed to be carried out because of a disturbance/blockage of the gas flow in the first gas duct. This means that the switching mechanism is advantageously designed to detect/to identify a disturbance/blockage in the first gas duct. For this purpose, the switching mechanism can comprise a measuring device which can be designed to detect a pressure, a volume and/or a flow rate of the gas flow of the first gas duct. The switching mechanism can be designed to automatically switch on the basis of a detected rise in pressure or volume for a predetermined period of time. As a result, removal of gas/respiratory gas automatically is guaranteed in the event of a blockage/disturbance of the first gas duct. The switching mechanism can optionally be switchable continuously and smoothly. This affords the advantage that the opening of the bypass of the nonreturn valve can be controlled into an intermediate position.

In a further development, the switching modes can be selected and can be adjusted via the switching mechanism. As a rule, at least two switching modes are preset in the switching mechanism. The switching modes can optionally be adjustable or selectable by technical personnel via a blocking function of the switching mechanism. Handling technical personnel can thus also control the switching mechanism outside the preset switching modes or can set up and store an adapted switching mode for a patient.

In one refinement, the gas control device comprises a first gas duct and a second gas duct, wherein the gas flow can be removed from the first gas duct. The first gas duct is generally designed as an inspiration branch which supplies a respiratory gas to a patient. However, in the case of a leakage hose system, the first gas duct is also reached by backflowing respiratory gas from the patient, said respiratory gas having to be removed. By the switching mechanism being switched into the first switching mode, the gas can be removed from the gas duct via the opening. In the case of a valve hose system, the first gas duct is closed in expiration by the nonreturn valve. For this purpose, the second gas duct is generally charged with a working pressure such that the sealing membrane is pressed onto the opening, and the gas of the first gas duct cannot escape via the opening, but can be fed to the valve internal to the hose system. The valve internal to the hose system is optionally connected upstream of the nonreturn valve and thus formed on the pressure side of the ventilator.

In a further refinement, the switching mechanism is designed so as, in the first switching mode, to control the gas control device in such a manner that the gas flow can be conducted via an opening in the first gas duct, on which opening a sealing membrane rests, to an intake side of the blower. The gas in the first gas duct is thus advantageously removed remote from the patient. As a rule, the gas removed through the opening can be conducted in a bypass duct to the intake side. Alternatively, the removed gas can be fed again to the first gas duct via the bypass duct.

In a development of the invention, the switching mechanism in the first switching mode is designed to conduct the gas flow of the first gas duct past a nonreturn valve. In the event of use of a valve hose system, a ventilator generally has a nonreturn valve for protecting the ventilator against recycled, contaminated exhaled gas of the patient. A disadvantage of such nonreturn valves is that, in the event of a blockage/disturbance of the active exhaling valve, said nonreturn valves obstruct exhaling of a patient or completely prevent same. The switching mechanism is therefore advantageously arranged in the ventilator in such a manner that a nonreturn valve can be bypassed by conducting gas from the opening of the first gas duct into the bypass path.

In a further development, the switching mechanism is designed to control the gas control device in the second switching mode in such a manner that the sealing membrane is charged with a working pressure from the patient. As a rule, the first gas duct is connected to the second gas duct, wherein the second gas duct can be charged with a working pressure. The working pressure is provided as a rule by the switching mechanism.

The switching mechanism can also be designed to be switchable in a variable manner, wherein the switching mechanism can be designed to infinitely variably control a pressure of the gas flow and the second gas duct between 0 mbar and 1 bar, in particular between 0 mbar and 100 mbar. The switching mechanism can also be designed to increase the gas flow/pressure in the second gas duct continuously for a predetermined period of time to a predetermined value.

In one refinement, the switching mechanism is designed to change the switching mode when required in the event of a change of a hose system. The gas control device is generally designed to identify a hose system change, wherein the switching mechanism of the gas control device is designed to switch into the corresponding switching mode on the basis of the identified hose system. The hose system is generally determined by an evaluation of respiratory gas parameters detected by a sensor of the switching mechanism. Alternatively, the hose system used can be identified manually by the patient or operational technical personnel via a user interface of the ventilator.

In a further refinement, the gas control device is arranged in the inspiration flow direction upstream of the blower. This affords the advantage that the gas control device is arranged with the switching mechanism on the intake side of the ventilator. Alternatively, the gas control device can be arranged on the pressure side of the ventilator, i.e. downstream of the blower in the inspiration flow direction. This provides an alternative arrangement option, which contributes to greater freedom of design in the arrangement of the gas control device in the ventilator.

The present invention furthermore comprises a ventilator comprising a gas control device according to at least one of the aforementioned features. Within the context of the invention, gas can be any breathable gas or gas mixture. In particular air, oxygen, expiration respiratory gas or inspiration expiratory gas.

Preferred exemplary embodiments of the invention will be explained in more detail below with reference to greatly simplified, schematic illustrations, in which:

BRIEF DESCRIPTION OF THE DRAWINGS

In the Figures, the same structural elements each have the same reference numbers.

DETAILED DESCRIPTION OF EMBODIMENTS OF THE INVENTION

Figure 1:
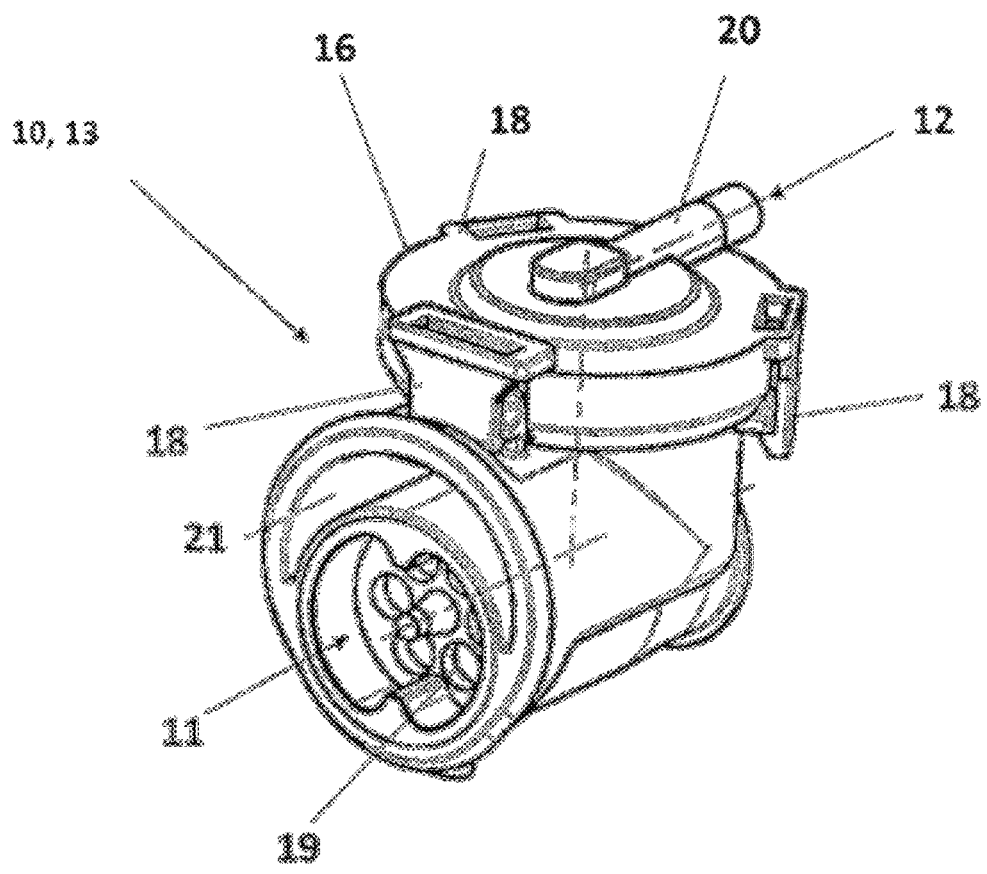
FIG. 1 shows a schematic view of a gas control device according to the invention, wherein the gas control device is only partially illustrated here, namely as a switching mechanism or as a valve block.

FIG. 1 shows a schematic view of a gas control device 10 according to the invention for a ventilator, wherein only a valve block or a switching mechanism 13 that is part of the gas control device is illustrated here.

The switching mechanism 13 according to the invention which is shown in FIG. 1 is provided for use in a ventilator for use with a leakage hose system and/or a valve hose system and/or a two-hose system, and has a first gas duct 11 (inspiratory branch) which conducts a gas flow in the direction of a patient. The first gas duct 11 comprises a nonreturn valve 19 and an opening (not shown) with a sealing membrane (not shown). The opening and the sealing membrane are concealed in FIG. 1 by a closure cap 16. The nonreturn valve 19 prevents a respiratory gas/gas flow coming from the patient from returning in the direction of the ventilator.

In addition, the switching mechanism 13 has a second gas duct 12 which conducts a pressure to the sealing membrane (not shown) on the opening (not shown). The second gas duct 12 is connected via a connection 20 to a closure cap 16 which is clipped onto the opening of the first gas duct 11. The second gas duct 12 runs via the connection 20 to the closure cap 16 and is controlled by a switching mechanism (not shown). A gas flow can flow through the second gas duct 12.

The switching mechanism can charge the second gas duct 12 with a working pressure or can keep same charge-free. In a predetermined operating state of the ventilator, the second gas duct 12 is charged with a working pressure, and therefore the charged gas flow or pressure is conducted via the connection 20 to the sealing membrane (not shown) within the closure cap 16. By means of the charged gas flow/pressure of the second gas duct 12, the sealing membrane is pressed completely onto the opening and the opening is thus closed.

FIG. 1 furthermore illustrates the bypass duct 21. The bypass duct 21 extends from the opening and permits the gas flow being discharged from the opening to be conducted past the nonreturn valve 19. The bypass duct 21 is designed to encircle the opening and tapers in its further course to form a duct which extends in a direction parallel to the first gas duct 11. The bypass duct 21 can subsequently open again into the first gas duct 11 or, as a separate branch, can remove the gas flow conducted past the nonreturn valve 19. The bypass duct 21 has an edge in the region of the opening (not shown), at which edge the sealing membrane can be sealed by the closure cap 16. The edge of the bypass duct 21 can have a protrusion, behind which an edge of the sealing membrane can engage. The edge of the bypass duct 21 prevents the sealing membrane from slipping.

In addition, the closure cap 16 is illustrated in FIG. 1. In the present embodiment, the closure cap 16 comprises three extensions 18, by means of which the closure cap 16 can be clipped onto the opening of the first gas duct 11. In addition, a connection 20 is formed on the closure cap 16, to which connection the second gas duct 12 can be connected. The connection 20 is arranged centrally on the closure cap 16, and the flow/pressure can be applied therefore gas centrally and uniformly to the sealing membrane via the connection 20 and the closure cap 16.

The switching mechanism described above is switched by means of the gas control device 10. As a rule, the switching mechanism switches the second gas duct 12 in a charge-free manner as soon as the ventilator switches over to expiration. In this case, no working pressure is fed to the gas flow of the second gas duct 12.

Conversely, the switching mechanism switches the second gas duct 12 in a manner free from working pressure/in a charge-free manner when the ventilator switches to inspiration.

The above-described gas control device can be employed for different uses. In the case of a leakage hose system, the switching mechanism is designed to switch the gas flow of the second gas duct 12 in a charge-free manner. In this case, the switching valve is designed to permanently permit a discharge of gas.

In the case of a valve hose system, the switching mechanism is designed to switch in accordance with the time-controlled expiration of the ventilator. The switching mechanism can thus switch the second gas duct 12 in a charge-free manner, for example during switching of the ventilator to expiration or in the event of a blockage of the expiratory branch. Expiration of a patient is thereby ensured since the opening of the gas control device 10 is opened during the expiration and a backflowing gas can escape via the opening.

During operation in the valve hose system, the switching mechanism switches the second gas duct 12 with the working pressure. By means of the charged pressure in the second gas duct 12, the sealing membrane is sealed on the opening, as a result of which a discharge of inspiratory gas through the opening is prevented during this type of operation.

In general, the gas control device 10 is designed during the inspiration to conduct the gas flow in the first gas duct 11 through the nonreturn valve 19 toward the patient. In the expiration, the opening of the first gas duct 11 is therefore closed and the nonreturn valve 19 continues to operate.

By contrast, in the event of a blockage/disturbance of an expiratory branch of the ventilator, exhalation of the patient is prevented or made difficult. In addition, the patient cannot exhale via the inspiratory branch because of the nonreturn valve 19. In the event of a blockage/disturbance of the expiratory branch of the ventilator, the switching mechanism is therefore designed to switch the second gas duct 12 in a charge-free manner. Since the second gas duct 12 is not charged with a working pressure that also acts on the sealing membrane, the gas flow of the first gas duct 11 can raise the sealing membrane that is resting on the opening. The gas flow of the first gas duct 11 can thereby be guided around the nonreturn valve 19 via a bypass duct 21.

Figure 2:
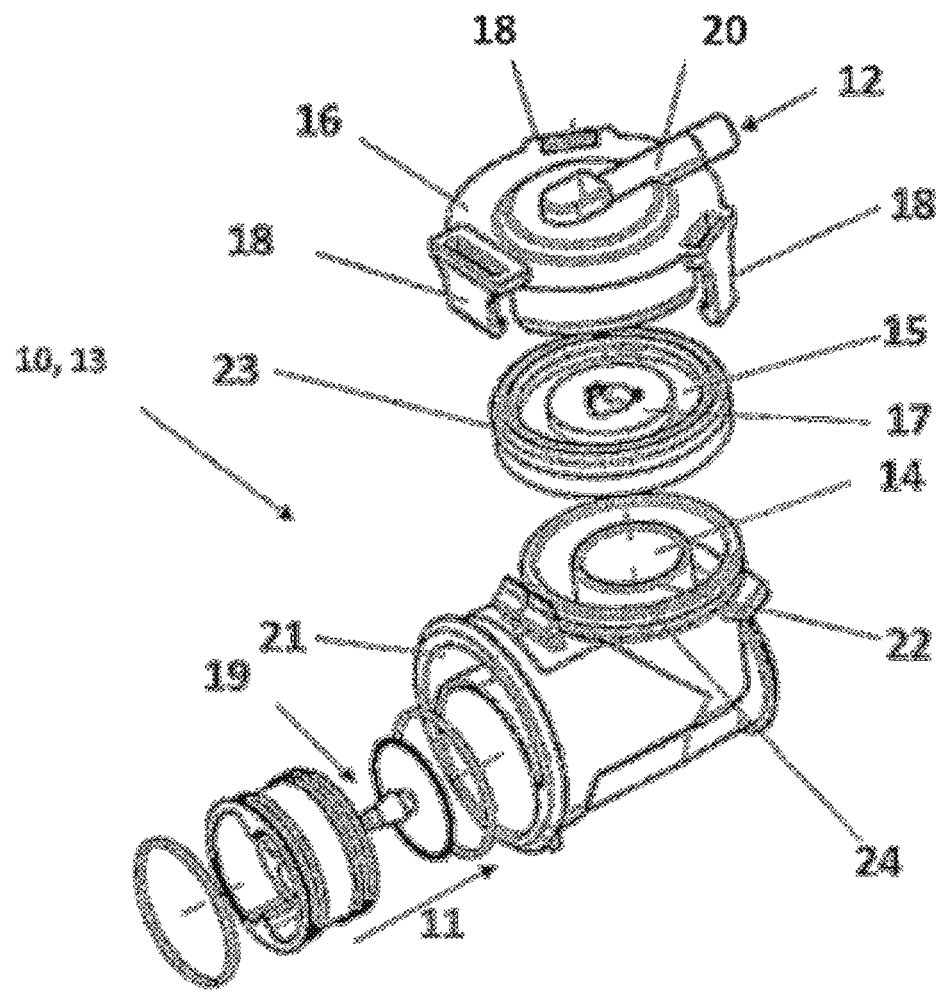
FIG. 2 shows a schematic exploded view of the switching mechanism/valve block shown in FIG. 1.

FIG. 2 shows a schematic exploded view of the switching mechanism 13 shown in FIG. 1. The first and the second gas ducts 11, 12, the nonreturn valve 19 and the opening 14 with the sealing membrane 15 are shown here.

The closure cap 16 with the connection 20 is also illustrated. The central arrangement of the connection 20 is shown, wherein one end of the connection 20 extends outward and can be connected to the second gas duct 12.

It is shown in FIG. 2 that the opening 14 has an edge 22. The edge 22 is designed as an elevation and serves as a rest for the weight 17 integrated in the sealing membrane 15.

The sealing membrane 15 is formed from an elastomeric material, preferably a silicone with a Shore A hardness of between 15 and 25, in particular a Shore A hardness of between 18 and 22. The sealing membrane 15 is circular and has a boundary 23.

The boundary 23 can be designed as a reinforced structure or as a functional protrusion. The boundary 23 is designed to rest on an edge 24 of the bypass duct 21. The sealing membrane 15 can have a thinner material thickness between the boundary 23 of the sealing membrane 15 and the weight 17 than in the region of the edge 24 of the bypass duct 21 and the edge of the sealing membrane 15, in which region the weight 17 is arranged, mostly integrally.

In the present embodiment, the sealing membrane 15 has a curved structure between the edge 24 of the bypass duct 21 and the weight 17, said curved structure additionally being able to prevent displacement of the sealing membrane 15 on the opening 14. In further embodiments, the sealing membrane 15 can have a different structure or can be structure-free between the edge 24 of the bypass duct 21 and the weight 17.

The weight 17 of the sealing membrane 15 is in the form of a plain washer. The weight 17 is formed from a metal and is formed integrally in the sealing membrane 17. The weight 17 can stabilize the sealing membrane 15 on the opening 14. As a rule, the weight 17 serves to prevent vibrations of the sealing membrane 15 by means of gas being discharged from the first gas duct.

The closure cap 16 shown in FIG. 2 comprises extensions 18 which form barbed hooks. When the closure cap 16 is clipped on, the barbed hooks engage in recesses which are formed on the outer side of the gas control device 10. In further embodiments, further closure options are conceivable, for example latching in the form of a bayonet catch.

When the closure cap 16 is placed onto the opening 14, the sealing membrane 15 in the region of the boundary 23 of the sealing membrane 15 is pressed onto the edge of the bypass duct 21 and held. The closure cap 16 seals off the sealing membrane 15 to the outside and holds the sealing membrane 15 in its position inside the closure cap 16. The sealing membrane 15 is thus pressed on/held on the edge 24 of the bypass duct 21 inside the gas control device 10 by means of the clipped-on closure cap 16. The sealing membrane 15 is clamped/sealed between the edge 24 of the bypass duct 21 and the closure cap 16 via the reinforced boundary 23 formed in an encircling manner.

Regions of the sealing membrane 15 that differ from the boundary 23 are formed in a contact-free manner with respect to the closure cap 16. Said regions may also be referred to as charging regions since the switching mechanism charges these regions of the sealing membrane 15 with the charged operating pressure supplied via the second gas duct.

In an inoperative state (without gas flows), the sealing membrane 15 is held by the weight and its structure on the opening 14. In the event of a disturbance or an expiration, the switching mechanism is designed to charge the second gas duct 12 with a working pressure.

If, by contrast, the switching mechanism is designed to hold/to switch the second gas duct 12 in a charge-free manner, the charging regions of the sealing membrane 15 are not charged with a gas flow, and therefore the gas flow of the first gas duct 11 is sufficient for lifting the sealing membrane in the region of the charging regions and for conducting the gas flow into the bypass duct 21.

Furthermore, the nonreturn valve 19 and the bypass duct 21 are illustrated in FIG. 2.

Figure 3:
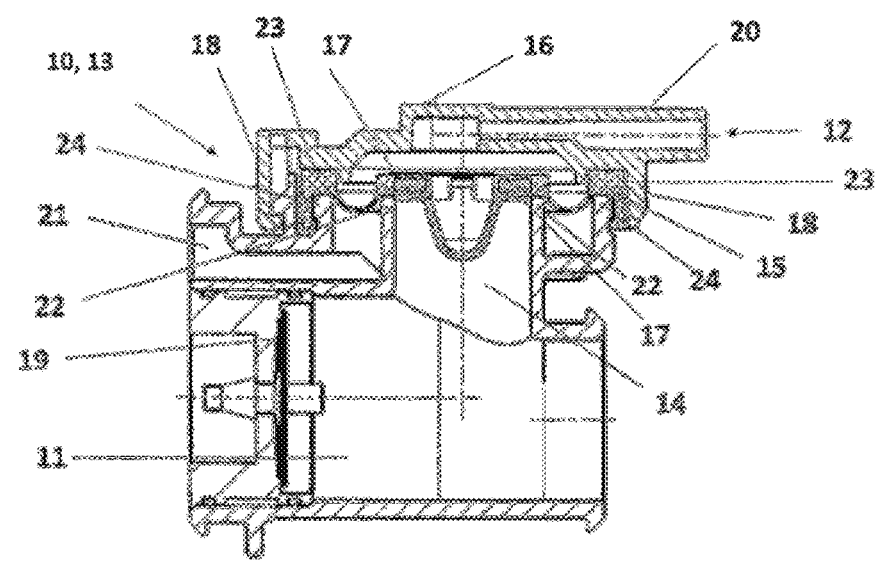
FIG. 3 shows a longitudinal section through the switching mechanism/valve block shown in FIGS. 1 and 2.

FIG. 3 shows a longitudinal section through the switching mechanism 13 shown in FIGS. 1 and 2. The first gas duct 11 with the nonreturn valve 19, the opening 14 and the sealing membrane 15 and also the second gas duct 12 are illustrated. In addition, the closure cap 16 with the connection 20 and the bypass duct 21 are illustrated.

An inspiratory gas flow can be conveyed to the patient via the first gas duct 11. The nonreturn valve 19 prevents exhaled gas from flowing back into the ventilator via the first gas duct 11. In the event of a blockage/disturbance of the expiratory branch of the ventilator, no expiration of the gas flow/exhaled gas can therefore take place via the first gas duct 11.

The bypass duct 21 which extends from the opening 14 is also shown. The bypass duct 21 is designed as an encircling duct around the opening 14 and extends in its further profile to a duct which extends in a direction parallel to the first gas duct 11. By means of the encircling arrangement of the bypass duct, a large amount of exhaled gas can be simultaneously conducted around and past the nonreturn valve 19 and removed via the opening 14. The bypass duct 21 can open into the inspiratory branch or can be configured as a separate branch.

The sealing membrane 15 is circular and has a weight 17 in its center. The weight 17 is ring-shaped/has the form of a plain washer. In its shape-induced cutout, the weight 17 has a conical configuration of the sealing membrane 15 that extends in the direction of the first gas channel 11. The conical configuration affords the advantage that the sealing membrane 15 is secured in its position on the opening 14 against slipping. In addition, it provides the patient with an installation aid regarding the orientation of the sealing membrane 15.

In further embodiments, the configuration of the sealing membrane 15 can have a different geometrical shape which is suitable for holding the sealing membrane 15 in its position. The weight 17 is integrated in the sealing membrane 15. The sealing membrane 15 has a greater material thickness in the region of the weight 17. This firstly affords the advantage that the weight 17 can be integrated in the sealing membrane 15 and secondly the greater material thickness produces an additional weight 17 that holds the sealing membrane 15 in its position. The weight 17 can also be applied to the sealing membrane 15.

The closure cap 16 shown in FIG. 3 is arranged on the opening 14, wherein the closure cap 16 in the region of the boundary 23 presses the sealing membrane 15 onto the edge of the bypass duct 21 while the sealing membrane 15 is arranged in the charging regions in a contact-free manner with respect to the closure cap 16.

Figure 4A:
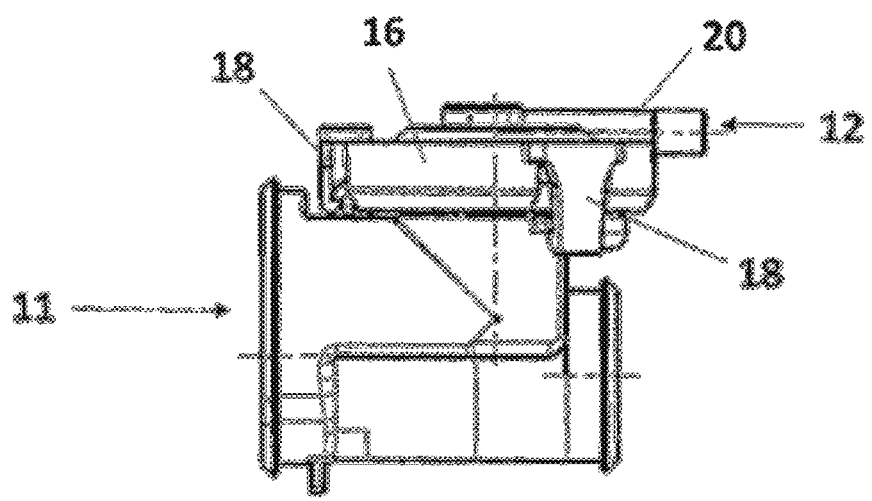
FIG. 4a shows a side view of the switching mechanism/valve block shown in FIGS. 1 to 3.

FIG. 4a shows a side view of the switching mechanism 13 shown in FIGS. 1 to 3. The first gas duct 11 and the closure cap 16 with the extensions 18 and the connection 20 for the second gas duct (not shown) are illustrated.

It can be seen in FIG. 4a that the inlet side of the first gas duct 11 is of a larger size than the outlet side. In addition to the first gas duct 11, the inlet side also comprises the bypass duct 21 which is narrowed to form a duct. The inlet side of the first gas duct 11 therefore comprises both the first gas duct 11, which is oriented in the inspiration flow direction, and the bypass duct 21, which is oriented counter to the inspiration flow direction.

Figure 4B:
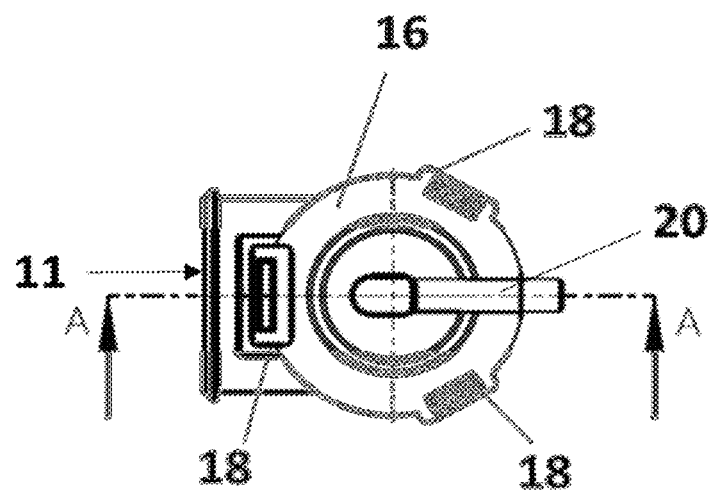
FIG. 4b shows a top view of a closure cap, according to the invention, of the switching mechanism/valve block shown in FIGS. 1 to 4a, FIG. 4c shows a side view of a nonreturn valve of the switching mechanism/valve block shown in FIGS. 1 to 4b.

FIG. 4b shows a top view of the closure cap 16 according to the invention of the switching mechanism 13 according to the invention which is shown in FIGS. 1 to 4b. The closure cap 16 can be clipped onto the opening (not shown) of the first gas duct. When the closure cap 16 is clipped on, the sealing membrane is pressed in the region of the weight (not shown) of the closure cap 16 onto an elevation 22 (shown in FIG. 3) of the opening and sealed.

The closure cap 16 has a connection 20 for a second gas duct 12 (not shown). The gas flow of the second gas duct 12 (not shown) can be applied to the sealing membrane (not shown) via the connection 20 in order to close the opening (not shown). The closure cap 16 furthermore comprises the extensions 18 which mostly form barbed hooks and are designed to engage in recesses in the region of the opening. In further embodiments, the closure cap 16 can have further extensions 18 or can be fastened on the opening via similar latching elements.

Figure 4C:
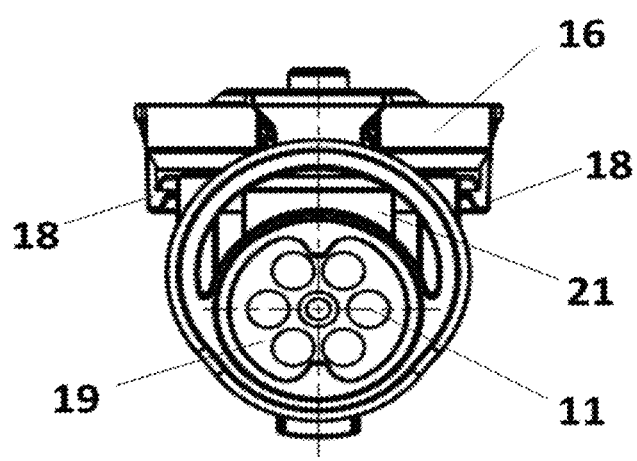

FIG. 4c shows a top view of the nonreturn valve 19 of the gas control device 10 according to the invention which is shown in FIGS. 1 to 4b. The view here is of the nonreturn valve 19 from the direction of the inflowing gas flow, in the inspiration flow direction. Also shown is the bypass duct 21 via which the gas flow can be conducted around the nonreturn valve 19 in the event of a blockage/disturbance of the expiratory branch of the ventilator.

The closure cap 16 is also illustrated in a side view with the extensions 18, by means of which the closure cap 16 can be clipped onto the opening (not shown).

FIGS. 5 to 13 show various embodiments of pneumatic switching arrangements of a ventilator according to the invention as part of a gas control device according to the invention.

Figure 5:
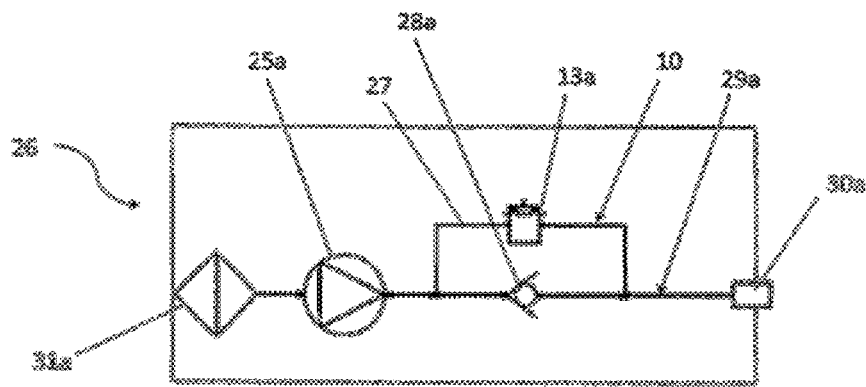
FIG. 5 shows an embodiment of a schematic design of a pneumatic switching arrangement of the gas control device according to the invention.

FIG. 5 shows an embodiment of a schematic design of a pneumatic switching arrangement of a ventilator 26 according to the invention comprising a gas control device 10 according to the invention. The pneumatic arrangement of the ventilator 26 comprises an inspiratory respiratory gas path 29a with a bypass 27 and a nonreturn valve 28a. Such pneumatic arrangements are generally used in a leakage hose system. The inspiratory respiratory gas path 29a comprises an appliance inlet 31a and an appliance outlet 30a. The appliance outlet 30a is arranged here close to the patient and the appliance inlet 31a is arranged remote from the patient. The respiratory gas path 29a extends from the appliance inlet 31a to the appliance outlet 30a. The respiratory gas path 29a comprises a respiratory gas drive 25a and the gas control device 10 with the nonreturn valve 28a and the switching mechanism/the switching valve 13a. In the gas control device 10 according to the invention, the switching mechanism 13 is arranged in a bypass 27 of the nonreturn valve 28a. The bypass 27 branches off between the respiratory gas drive 25a and the nonreturn valve 28a and opens again into the inspiratory respiratory gas path 29a between the nonreturn valve 28a and the appliance outlet 30a. The respiratory gas drive 25a is arranged between the appliance inlet 31a and the nonreturn valve 28a. Respiratory gas can be returned in the direction of the appliance inlet 31a via the switching mechanism 13a arranged in the bypass 27, thus bypassing the nonreturn valve 28a.

Figure 6:
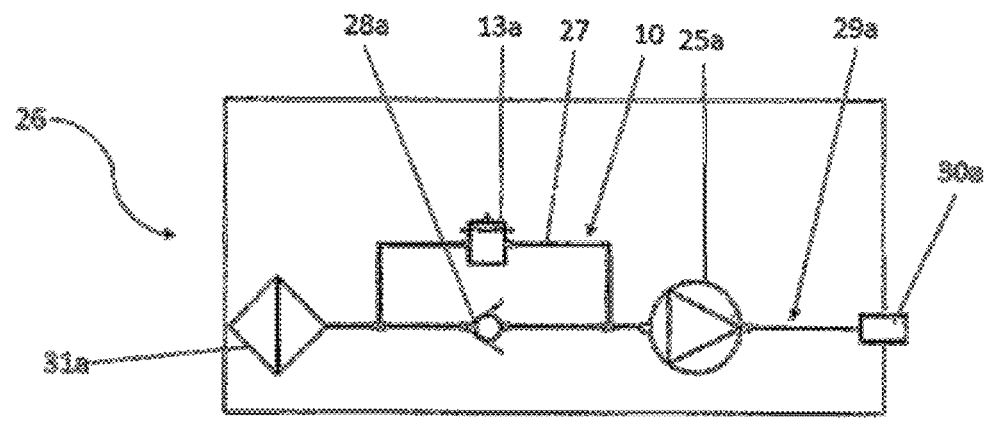
FIG. 6 shows an embodiment of a schematic design of a further pneumatic switching arrangement of the gas control device according to the invention.

FIG. 6 shows a further embodiment of a schematic design of a pneumatic switching arrangement of the ventilator 26 according to the invention comprising the gas control device 10 according to the invention. Such an arrangement is generally used in a leakage hose system. The ventilator 26 according to the invention with the inspiratory respiratory gas path 29a, with the bypass 27 around the nonreturn valve 28a, is shown. The inspiratory respiratory gas path 29a comprises the appliance inlet 31a and the appliance outlet 30a. The respiratory gas path 29a extends from the appliance inlet 31a to the appliance outlet 30a. The respiratory gas path 29a comprises the respiratory gas drive 25a and the gas control device 10 with the nonreturn valve 28a and the switching mechanism/the switching valve 13a. The switching mechanism 13a is arranged in the bypass 27 of the nonreturn valve 28a. In this alternative arrangement, the bypass 27 branches off between the appliance inlet 31a and the nonreturn valve 28a and leads again into the inspiratory respiratory gas path 29a between the nonreturn valve 28a and the respiratory gas drive 25a. The respiratory gas drive 25a is arranged between the nonreturn valve 28a and the appliance outlet 30a. Respiratory gas can be returned in the direction of the appliance inlet 31a via the switching mechanism 13a arranged in the bypass 27 after said respiratory gas has passed the respiratory gas drive 25a.

Figure 7:
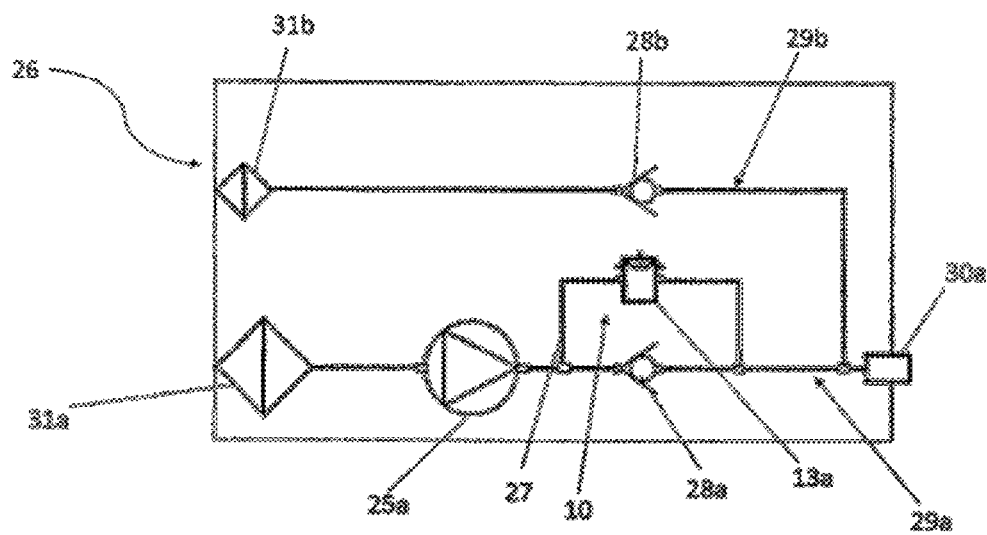
FIG. 7 shows an embodiment of a schematic design of a further pneumatic switching arrangement of the gas control device according to the invention.

FIG. 7 shows a further embodiment of a schematic design of a pneumatic switching arrangement of the ventilator 26 according to the invention comprising the gas control device 10 according to the invention. Such an arrangement can be used in a valve hose system. The ventilator 26 according to the invention with the inspiratory respiratory gas path 29a, the bypass 27 and a second inspiratory respiratory gas path 29b is shown. The inspiratory respiratory gas path 29a extends from the appliance inlet 31a to the appliance outlet 30a. The inspiratory respiratory gas path 29a comprises the respiratory gas drive 25a and the gas control device 10 with the nonreturn valve 28a and the switching mechanism 13a, wherein the switching mechanism 13a is arranged in the bypass 27 for bypassing the nonreturn valve 28a. The embodiment of the ventilator 10 that is shown in FIG. 7 has the second inspiratory respiratory gas path 29b which extends from a second appliance inlet 31b to the common appliance outlet 30a. The second inspiratory respiratory gas path 29b opens into the inspiratory respiratory gas path 28a between the nonreturn valve 28a and the common appliance outlet 30a. For example, in the event a of blockage/disturbance of the inspiratory respiratory gas path 29a, respiratory gas can be obtained by the separate appliance inlet 31b via the second inspiratory respiratory gas path 29b and supplied to the patient. In addition, in the event of a blockage of an expiratory respiratory gas path, respiratory gas can be returned through the switching mechanism 13a, by bypassing the nonreturn valve 28a, and the patient can be enabled to exhale.

Figure 8:
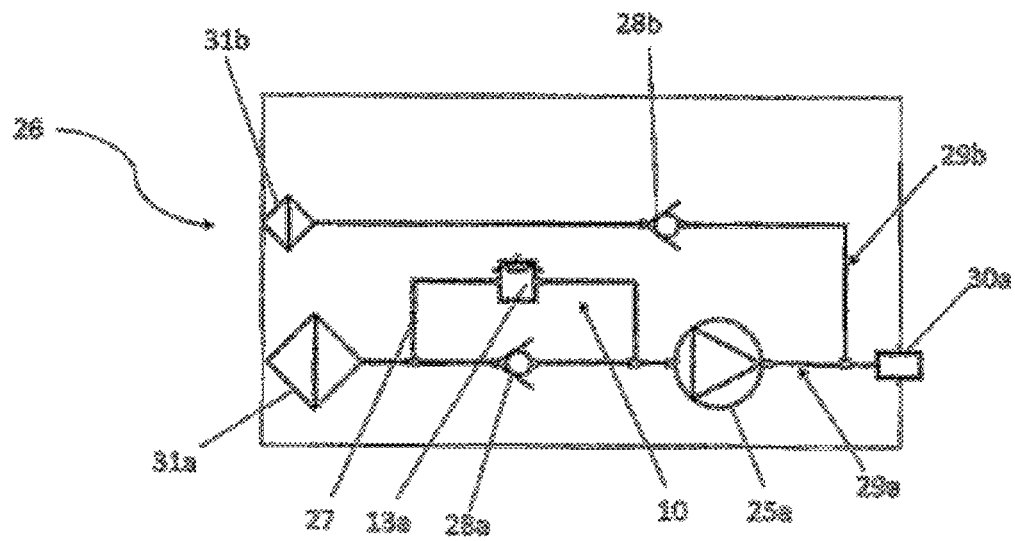
FIG. 8 shows an embodiment of a schematic design of a further pneumatic switching arrangement of the gas control device according to the invention.

FIG. 8 shows a further embodiment of a schematic design of a pneumatic switching arrangement of the ventilator 26 according to the invention comprising the gas control device 10 according to the invention. The ventilator 26 according to the invention with the inspiratory respirator gas path 29a, the bypass 27 and the second inspiratory respiratory gas path 29b is shown. In this alternative embodiment, the nonreturn valve 28a is arranged in the inspiratory respiratory gas path 29a between the appliance inlet 31a and the respiratory gas drive 25a. The bypass 27 is formed around the nonreturn valve 28a, the bypass branching off between the appliance inlet 31a and opening again into the inspiratory respiratory gas path 29a between the nonreturn valve 28a and the respiratory gas drive 25a. The respiratory gas drive 25a is arranged between the nonreturn valve 28a and the appliance outlet 30a. The second inspiratory respiratory gas path 29b opens into the inspiratory respiratory gas path 29a between the respiratory gas drive 25a and the common appliance outlet 30a. The second inspiratory respiratory gas path 29b can comprise a nonreturn valve 28b. Also in this embodiment, for example, in the event of a blockage/disturbance of the inspiratory respiratory gas path 29a, respiratory gas can be obtained by the separate appliance inlet 31b via the second inspiratory respiratory gas path 28b and supplied to the patient. In addition, similarly in the event of a blockage of an inspiratory respiratory gas path, respiratory gas can be returned through the gas control device with the switching mechanism 13a by bypassing the nonreturn valve 28a and the patient is enabled to exhale.

Figure 9:
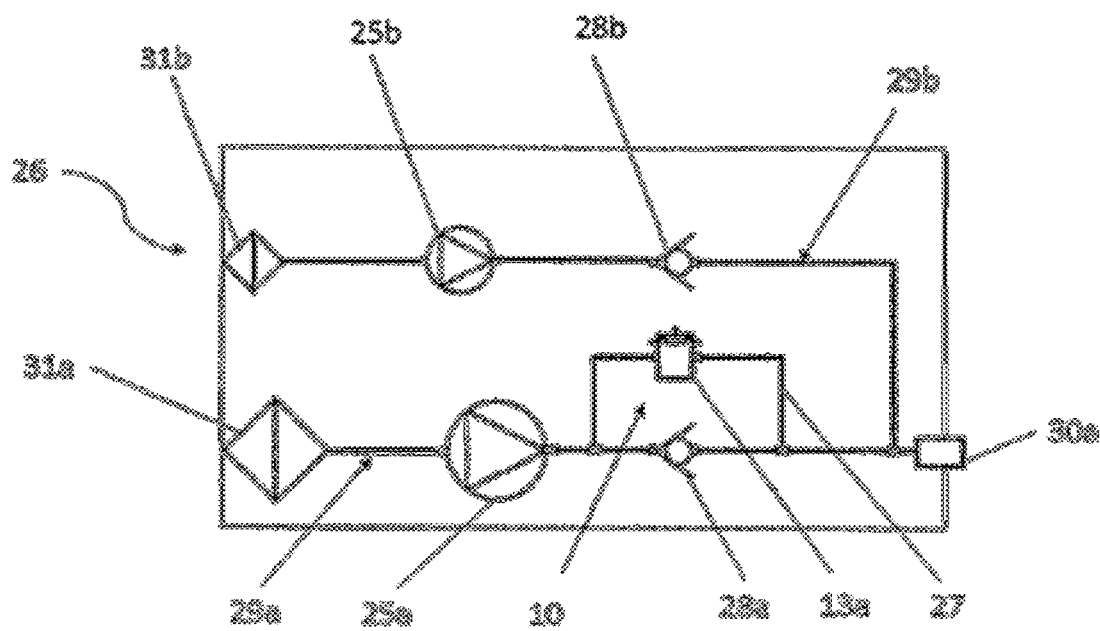
FIG. 9 shows an embodiment of a schematic design of a further pneumatic switching arrangement of the gas control device according to the invention.

FIG. 9 shows a further embodiment of a schematic design of a pneumatic switching arrangement of the ventilator 26 according to the invention comprising the gas control device 10 according to the invention. The ventilator 26 according to the invention with the inspiratory respiratory gas path 29a, the bypass 27 and the second inspiratory respiratory gas path 29b is shown.

The inspiratory respiratory gas path 29a extends from the appliance inlet 31a to the appliance outlet 30a and comprises the respiratory gas drive 25a and the gas control device 10 according to the invention with the nonreturn valve 28a and the switching mechanism 13a. The switching valve 28a is arranged in the bypass 27 for bypassing the nonreturn valve 28a. The bypass 27 is formed between the respiratory gas drive 25a and the appliance outlet 30a. The embodiment of the ventilator 26 that is shown in FIG. 9 likewise has the second inspiratory respiratory gas path 29b which extends from the second appliance inlet 31b to the common appliance outlet 30a. The second inspiratory respiratory gas path 29b opens into the inspiratory respiratory gas path 29a between the nonreturn valve 28b and the common appliance outlet 30a. The second inspiratory respiratory gas path 29b has a nonreturn valve 28b and a second respiratory gas drive 25b, wherein the respiratory gas drive 25b is arranged between the second appliance inlet 31b and the nonreturn valve 28b. In this embodiment, for example in the event of a blockage/disturbance of the inspiratory respiratory gas path 29a, respiratory gas can be obtained by the separate appliance inlet 31b via the second inspiratory respiratory gas path 29b and supplied to the patient. In addition, similarly in the event of a blockage of an expiratory respiratory gas path, respiratory gas can be returned via the switching valve 13a arranged in the bypass 27, bypassing the nonreturn valve 28a, and the patient is enabled to exhale.

Figure 10:
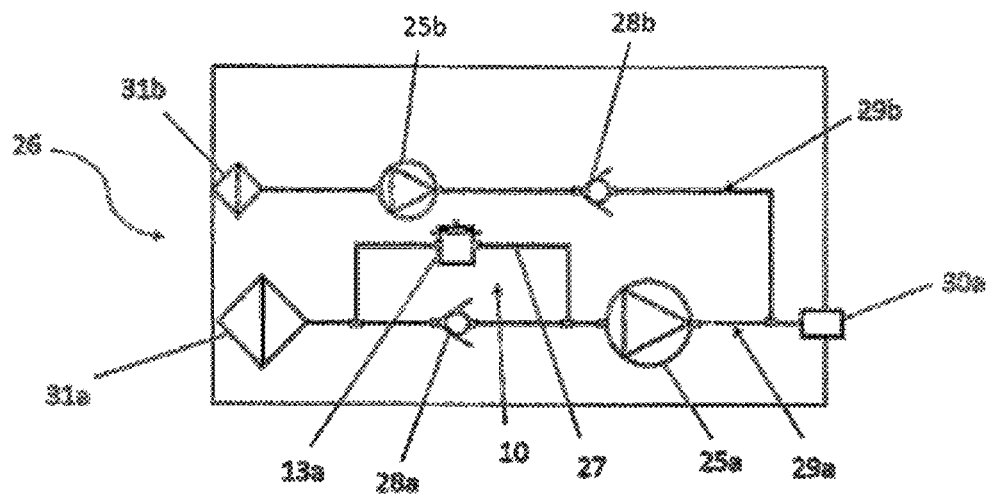
FIG. 10 shows an embodiment of a schematic design of a further pneumatic switching arrangement of the gas control device according to the invention.

FIG. 10 shows a further embodiment of a schematic design of a pneumatic switching arrangement of the ventilator 26 according to the invention comprising the gas control device 10 according to the invention. A ventilator 26 according to the invention with the inspiratory respiratory gas path 29a, the bypass 27 and the second inspiratory respiratory gas path 29b is shown. The inspiratory respiratory gas path 29a extends from the appliance inlet 31a to the appliance outlet 30a and comprises the gas control device 10 with the nonreturn valve 28a and the switching mechanism 13a, and also the respiratory gas drive 25a.

The switching mechanism 13a is arranged in the bypass 27 for bypassing the nonreturn valve 28b. The bypass 27 with the switching mechanism 13a is arranged between the appliance inlet 31a and the respiratory gas drive 25a. The embodiment of the ventilator 26 that is shown in FIG. 10 has the second inspiratory respiratory gas path 29b which extends from a second appliance inlet 31b to the common appliance outlet 30a. The second inspiratory respiratory gas path 29b opens into the inspiratory respiratory gas path 29a between the respiratory gas drive 25a and the common appliance outlet 30a. The second inspiratory respiratory gas path 29b has the nonreturn valve 28b and the respiratory gas drive 25b, wherein the respiratory gas drive 25b is arranged between the second appliance inlet 31b and the nonreturn valve 28b.

Figure 11:
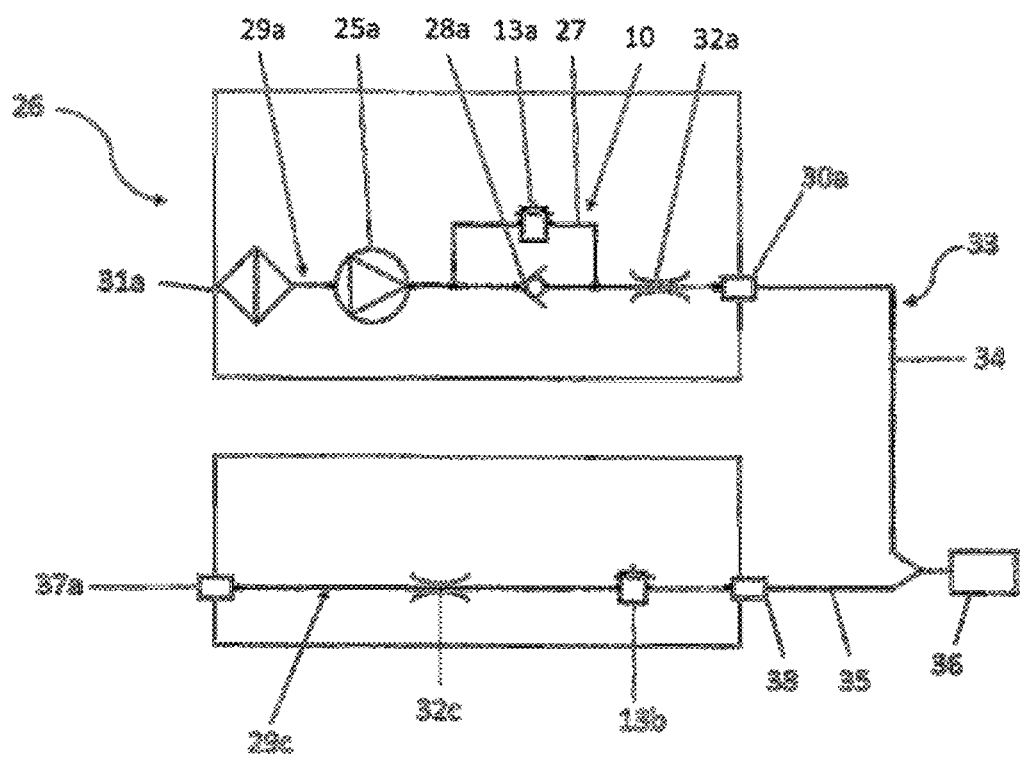
FIG. 11 shows an embodiment of a schematic design of a further pneumatic switching arrangement of the gas control device according to the invention.

FIG. 11 shows a further embodiment of a schematic design of a pneumatic switching arrangement of the ventilator 26 according to the invention comprising the gas control device 10 according to the invention. The ventilator 26 according to the invention with the inspiratory respiratory gas path 29a with a bypass 27, and with an expiratory respiratory gas path 29c, is shown.

The inspiratory respiratory gas path 29a extends from the appliance inlet 31a toward the appliance outlet 30a. The inspiratory respiratory gas path 29a here comprises the respiratory gas drive 25a and the gas control device 10 with the nonreturn valve 28a and the switching mechanism 13a, which is arranged in a bypass 27 of the nonreturn valve 28a, and a gas-measuring mechanism (flow and/or pressure) 32a. The gas-measuring mechanism 32a is arranged between the bypass 27 and the appliance outlet 30a. A flow or a volume or a pressure of the respiratory gas in the respiratory gas path can be detected by the gas-measuring mechanism 32a. At a predetermined volume or pressure of respiratory gas for a predetermined period of time, the switching mechanism 13a can be switched, for example, by means of a 3/2 way valve. The switching mechanism 13a is generally designed and configured to set a PEEP (positive end-expiratory pressure) in the range of 0-20 hPa, preferably 0-15 hPa.

The expiratory respiratory gas path 29c extends from an expiratory appliance inlet 38 to the expiratory appliance outlet 37a and comprises a switching mechanism 13b and a flow-measuring mechanism 32c. The flow-measuring mechanism 32c is arranged here between the expiratory appliance outlet 37a and the switching mechanism 13b. The flow-measuring mechanism 32c serves here for detecting a flow or a volume or a pressure of the respiratory gas in the respiratory gas path. Feedback about the volume of the respiratory gas, which is output by the patient, to the ventilator can take place on the basis of the values detected by the flow-measuring mechanism 32c.

A hose system 33 with a first branch 34 and a second branch 35 is adapted to the appliance outlet 30a. The first branch 34 leads from the appliance outlet 30a to a patient interface 36. From the patient interface 36, the hose system 33 leads with the second branch 35 to the expiratory appliance inlet 38 for expiratory respiratory gas. The patient interface 36 is connected to the inspiratory respiratory gas path 29a and to the expiratory respiratory gas path 29c via the hose system 33.

In the embodiment of the ventilator 26 that is shown in FIG. 11, a respiratory gas can be obtained via the appliance inlet 31a and can be conducted by the respiratory gas drive 25a via the nonreturn valve 28a in the direction of the appliance outlet 30a.

The respiratory gas is passed on by the appliance outlet 30a via the branch 34 of the adapted hose system 33 to the patient interface 36, via which a patient can inhale the respiratory gas. The exhaled gas from the patient can be supplied by the expiratory appliance inlet 38 via the branch 35 of the adapted hose system 33 to the respiratory gas path 29c. Via the expiratory respiratory gas path 29c, the respiratory gas is conducted to the expiratory appliance outlet 37a and output into the surroundings. In the event of a blockage/disturbance of the expiratory respiratory gas path 29c, the respiratory gas can be removed in the inspiratory respiratory gas path 29a by control of the switching mechanism 13a in the bypass 27.

Figure 12:
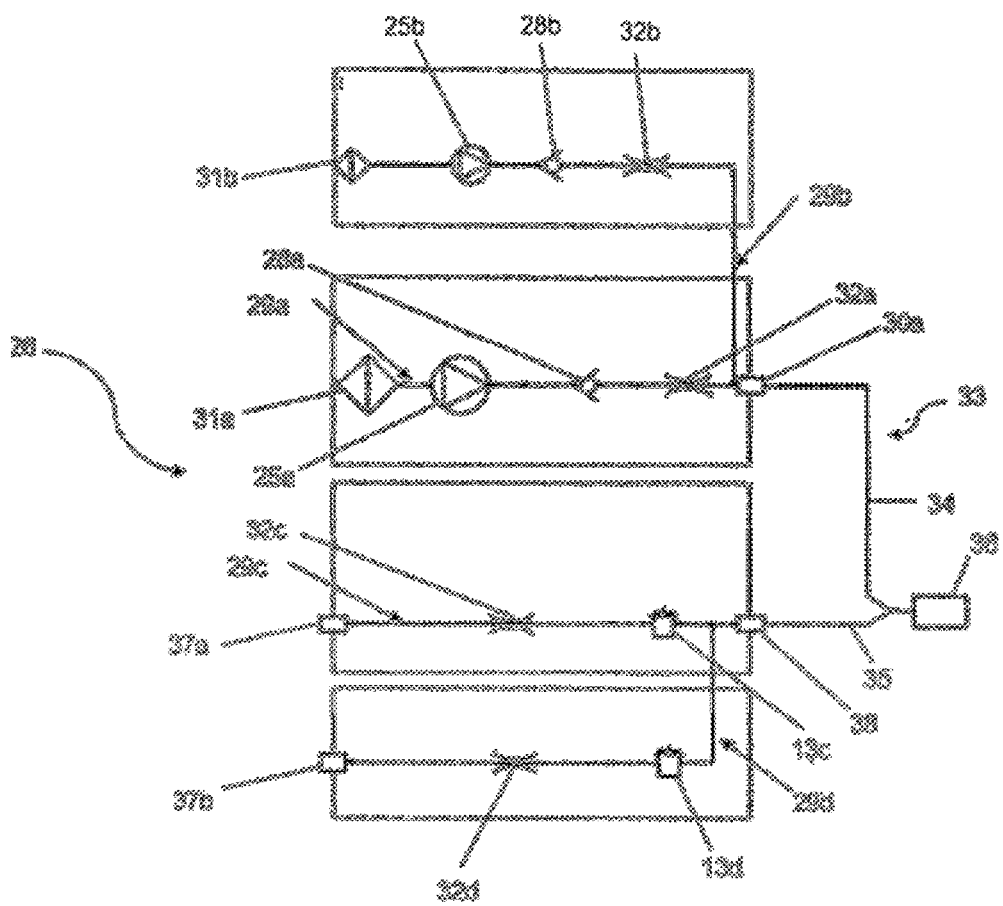
FIG. 12 shows an embodiment of a schematic design of a further pneumatic switching arrangement of the gas control device according to the invention, FIGS. 13-15 each show an embodiment of the gas control device according to the invention when different hose systems are used.

FIG. 12 shows a further embodiment of a schematic design of a pneumatic switching arrangement of the ventilator 26 according to the invention comprising the gas control device 10 according to the invention. A ventilator 26 according to the invention with the first inspiratory respiratory gas path 29a and the second respiratory gas path 29b and with the expiratory respiratory gas path 29c and a separate expiratory respiratory gas path 29d is shown.

The inspiratory respiratory gas path 29a extends from the appliance inlet 31a toward the appliance outlet 30a. The inspiratory respiratory gas path 29a comprises the respiratory gas drive 25a, the nonreturn valve 28 and a flow-measuring mechanism 32a. The flow-measuring mechanism 32a is arranged between the nonreturn valve 28a and the appliance outlet 30a. The flow-measuring mechanism 32a detects a flow or a volume or a pressure of the respiratory gas which is output to the patient via the inspiratory respiratory gas path 29a.

The embodiment of the ventilator 26 that is shown in FIG. 12 has a second inspiratory respiratory gas path 29b which extends from the second appliance inlet 31b to the common appliance outlet 30a. The second inspiratory respiratory gas path 29b opens into the inspiratory respiratory gas path 29a between the flow-measuring mechanism 32a and the common appliance outlet 30a. The second inspiratory respiratory gas path 29b can comprise the separate respiratory gas drive 25b, a nonreturn valve 28b and a flow-measuring mechanism 32b. The second respiratory gas drive 25b is arranged between the second appliance inlet 31b and the nonreturn valve 28b. The flow-measuring mechanism 32b can detect a volume or pressure of the inspiratory respiratory gas in the respiratory gas path 29b and can transmit same to the ventilator 26. In the event of a blocgade of the inspiratory respiratory gas path 29a, respiratory gas can be obtained by the appliance inlet 31b via the second inspiratory respiratory gas path 29b and supplied to the patient.

The embodiment of the ventilator 26 that is shown in FIG. 12 furthermore has the expiratory respiratory gas path 29c which extends from the expiratory appliance inlet 38 to the expiratory appliance outlet 37a and comprises the switching mechanism 13b and the flow-measuring mechanism 32c. The flow-measuring mechanism 32c is arranged here between the expiratory appliance outlet 37a and the switching mechanism 13b. The flow-measuring mechanism 32c detects a volume and/or a pressure of the respiratory gas output by the patient. A respiratory gas output by the patient can be removed via the expiratory respiratory gas path 29c.

The gas-measuring mechanisms 32a, 32b, 32c and 32d can be designed to detect a flow or a volume or a pressure of the respiratory gas in the respiratory gas path and, on the basis thereof, to switch or to open and to close a switching valve or to supply feedback to the ventilator 26 about the flow or the volume or the pressure of the respiratory gas supplied to the patient or respiratory gas output by the patient.

The embodiment, shown in FIG. 12, of the pneumatic arrangement in the ventilator 26 also has a separate expiratory respiratory gas path 29d. The second expiratory respiratory gas path 29d branches off from the expiratory respiratory gas path 29c and extends toward a separate appliance outlet 37b. The separate expiratory respiratory gas path 29d comprises a switching mechanism 14c and a flow-measuring mechanism 32d. The measuring mechanism 32d detects a flow or a volume or a pressure of the respiratory gas output by the patient. In the event of a blockage/disturbance of the expiratory respiratory gas path 29c, respiratory gas output by the patient can be removed via the separate expiratory respiratory gas path 16d.

A hose system 33 with a first branch 34 and a second branch 35 is adapted to the appliance outlet 30a. The first branch 34 leads from the appliance outlet 30a to a patient interface 36. From the patient interface 36, the hose system 33 with the second branch 35 leads to the expiratory appliance inlet 38 for expiratory respiratory gas. The patient interface 36 is connected to the inspiratory respiratory gas path 29a, the second inspiratory respiratory gas path 29b, the expiratory respiratory gas path 29c and the separate expiratory respiratory gas path 29d via the hose system 33c.

Figure 13:
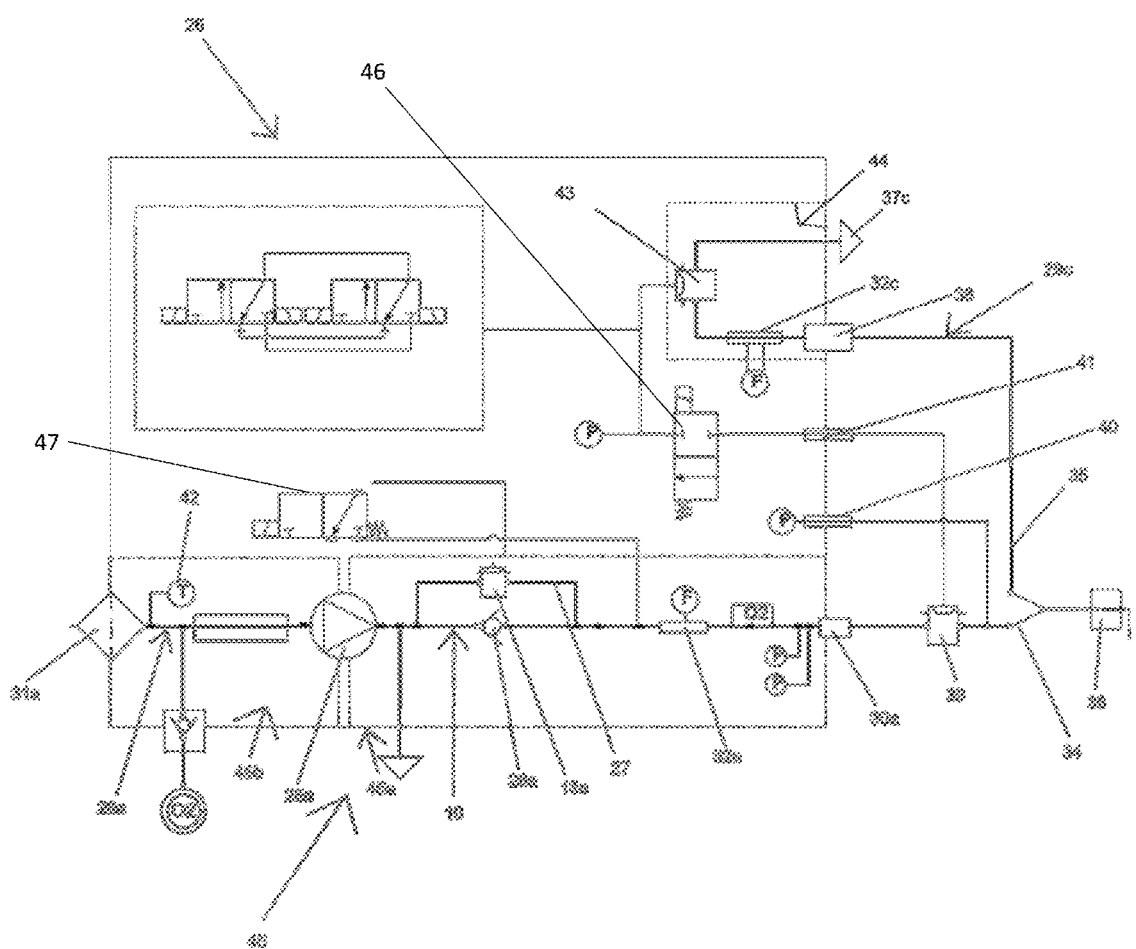
Figure 14:
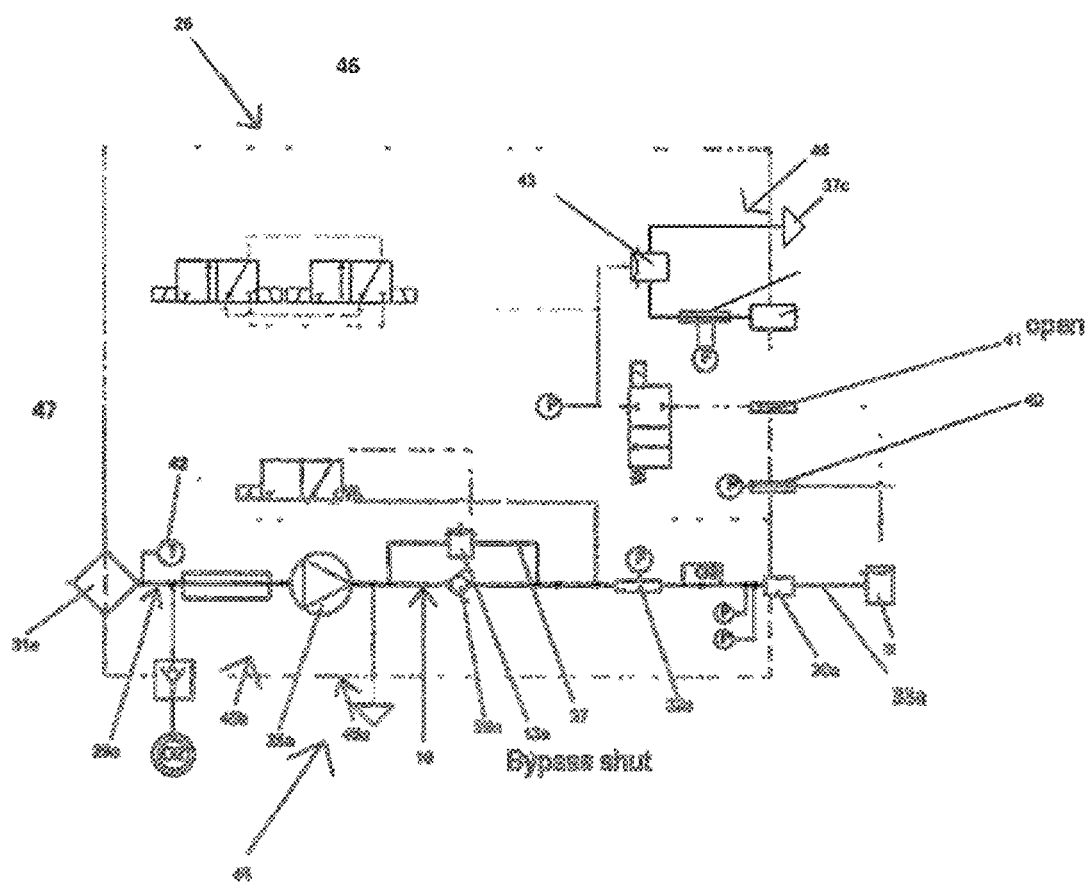
Figure 15:
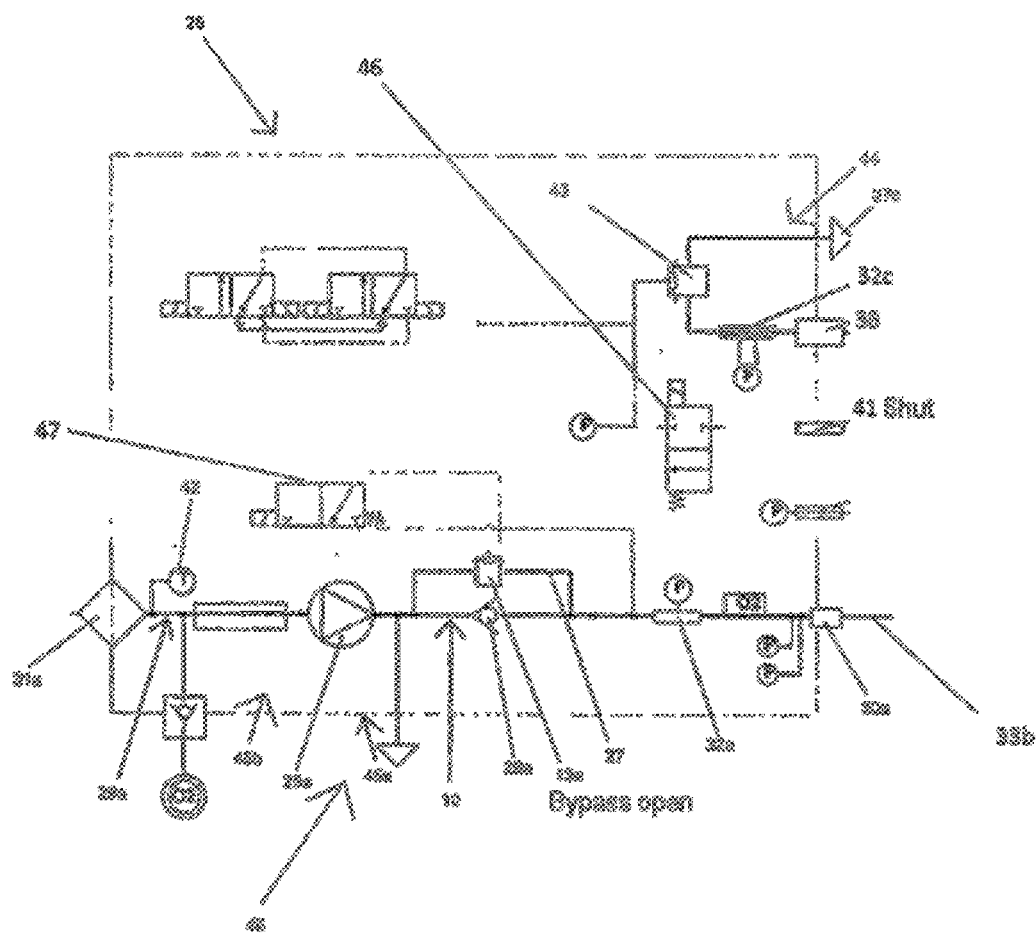

FIGS. 13-15 show a further embodiment of a schematic design of the ventilator 26 according to the invention comprising the gas control device 10 according to the invention.

A pneumatic switching arrangement comprising the inspiratory respiratory gas path 29b and the expiratory respiratory gas path 29c is shown.

The ventilator comprises a respiratory gas path 29c which extends between an appliance inlet 31a and an appliance outlet 30a, wherein the respiratory gas path 29a comprises a respiratory gas drive 25a and a gas control device 10 with a nonreturn valve 28a, a bypass 27 and a switching mechanism 13a, wherein the respiratory gas conducts an inspiratory drive 25a respiratory gas flow from the appliance inlet 31a through the nonreturn valve to the appliance outlet 30a, wherein the nonreturn valve is designed and arranged to prevent a respiratory gas flow (in the blocking direction of the nonreturn valve) in the direction of the appliance inlet 31a, and the bypass 27 is designed and arranged to permit a respiratory gas flow for bypassing the nonreturn flow 28a, and the switching device 13a is designed and arranged to at least temporarily permit or to interrupt a respiratory gas flow through the bypass 27 for bypassing the nonreturn valve 28a.

The respiratory gas flow runs through the bypass counter to the blocking direction of the nonreturn valve.

The switching mechanism 13a is arranged in the bypass 27, and the bypass 27 branches off from the respiratory gas path 29a upstream of the nonreturn valve 28a and opens again downstream of the nonreturn valve 28a into the respiratory gas path 29a or into the appliance inlet.

The respiratory gas drive 25a is arranged between the appliance inlet 31a and the nonreturn valve 28a.

The respiratory gas drive 25a can also be arranged between nonreturn valve 28a and the appliance outlet 30a.

The switching mechanism 13 is arranged in the bypass 27, and the bypass 27 branches off, for example, between the respiratory gas drive 25a and the nonreturn valve 28a and opens again into the respiratory gas path 29a between the nonreturn valve 28a and the appliance outlet 30a, wherein the respiratory gas drive 25a is arranged between the appliance inlet 31a and the nonreturn valve 28a and respiratory gas can be returned in the direction of the appliance inlet 31a via the switching mechanism 13a arranged in the bypass 27, by bypassing the nonreturn valve 28a.

A design is also conceivable in which the switching mechanism 13a is arranged in the bypass 27 and the bypass 27 branches off between the appliance inlet 31a and the nonreturn valve 28a and opens again into the respiratory gas path 29a between the nonreturn valve 28a and the respiratory gas drive 25a, wherein the respiratory gas drive 25a is arranged between the nonreturn valve 28a and the appliance outlet 30a and respiratory gas can be returned in the direction of the appliance inlet 31a via the switching mechanism 13a arranged in the bypass 27, after said respiratory gas has passed the respiratory gas drive 25a.

It is also conceivable for a second respiratory gas path 29b to lead from an appliance inlet 31a, 31b to the appliance outlet wherein 30a, the second respiratory gas opens path 29b into the first respiratory gas path 29a upstream of the appliance outlet and downstream of the nonreturn valve and downstream of the respiratory gas drive.

It is also conceivable that a nonreturn valve 29b and/or a respiratory gas drive 25b is arranged in the second respiratory gas path 29b in order to conduct a defined respiratory gas flow from the appliance inlet 31a, 31b to the appliance outlet 30a.

It is also conceivable that a gas-measuring mechanism 32a is arranged between the bypass 27 and the appliance outlet 30a and is designed to detect a flow or a volume or a pressure of the respiratory gas in the respiratory gas path, and the switching mechanism 13a is designed and configured to set a PEEP (positive end-expiratory pressure) in the range of 0-20 hPa, preferably 0-15 hPa.

It is also conceivable that the ventilator has an expiratory respiratory gas path 29c which extends from an expiratory appliance inlet 38 to an expiratory appliance outlet 37a and comprises a switching mechanism 13b and a gas-measuring mechanism 32c, wherein the gas-measuring mechanism 32c is arranged between the expiratory appliance outlet 37a and the switching mechanism 13b.

It is also conceivable that a hose system 33 is mounted on the appliance outlet 30a, wherein the hose system 33 has a first branch 34 and a second branch 35, wherein the first branch 34 leads from the appliance outlet 30a to a patient interface 36, and, from the patient interface 36, a second branch 35 leads to the expiratory appliance inlet 38, wherein inspiratory respiratory gas is conducted from the inspiratory respiratory gas path 29a to the patient interface 36 via the first branch 34, and expiratory respiratory gas is conducted from the patient interface 36 to the expiratory respiratory gas path 29a via the second branch 35.

It is also conceivable that, in the event of a blockage/disturbance of the expiratory respiratory gas path 29c, the expiratory respiratory gas can be removed by control of the switching mechanism 13a into the inspiratory respiratory gas path 29a and via the open bypass 27 into the surroundings.

It is also conceivable that the ventilator has a first inspiratory respiratory gas path 29a and a second inspiratory respiratory gas path 29b and also an expiratory respiratory gas path 29c and a separate expiratory respiratory gas path 29d.

The design of a switching arrangement that is shown in FIG. 13 is designed to conduct respiratory gas from the appliance inlet via the inspiratory respiratory gas path 29a to the appliance outlet 30a and to feed same to the patient via a hose system which is plugged onto the appliance outlet. If the hose system is a two-hose system 33c, exhaled respiratory gas from the patient is supplied via the branch 35 of the two-hose system 33c to the expiratory respiratory gas path 29c. For this purpose, the branch 35 of the two-hose system 33c is fastened to the inlet 38 of the ventilator.

The first branch 34 of the two-hose system 33c is fastened to the appliance outlet and delivers inspiratory respiratory gas to the patient interface 36.

The first branch 34 can comprise at least one separate branch which comprises a pressure sensor 40 and/or a patient valve connection. For example, the separate branch can branch off from the first branch 34 between a switching valve 39 and the convergence of the first branch 34 and the second branch 35.

The inspiratory respiratory gas path 29a extends from the appliance inlet 31a to the appliance outlet 30a. The inspiratory respiratory gas path 29b comprises the blower 25a and at least partially the gas control device 10 with the nonreturn valve 28a and the switching mechanism 13a. In the present embodiment, the inspiratory respiratory gas path 29a also comprises a temperature sensor 42, at least one flow-measuring mechanism 32a and/or at least one pressure sensor 40. The inspiratory respiratory gas path 29a can be arranged in an inspiratory block 45, wherein the inspiratory block 45 comprises a pressure side 45a and a suction side 45b.

The expiratory respiratory gas path 29c extends from the second branch 35, if the two-hose system is connected, in the direction of an expiratory appliance outlet 37b. The expiratory respiratory gas path 29c here comprises an expiratory appliance inlet 38, a flow-measuring mechanism 32c, an internal patient valve 43 and an expiratory appliance outlet 37c. In the present embodiment, the expiratory respiratory gas path 29c is arranged in an expiratory block 44. The expiratory block 44 can optionally be controlled separately from the inspiratory block 45 or can be removed from the ventilator 26.

The gas control device 10 is, for example, designed and configured to control the inspiratory block 45 and the expiratory block.

The ventilator is designed for use with alternative hose systems 33, wherein the ventilator comprises at least one respiratory gas source 25, at least one respiratory gas path 27, 29, at least one appliance outlet 30, and an appliance inlet 31, and a gas control device 10 for presetting the ventilator for use of the alternative hose systems 33 by switching at least one switching mechanism 13, 46, 47, wherein, for use:
  of a leakage system 33b the gas control device (10) activates the switching mechanism 13a, 47 to open the respiratory gas path 27 (bypass) for a respiratory gas flow
  of a valve system 33a with a patient valve 39, the gas device control (10) activates the switching mechanism 13a, 47 to block a respiratory gas flow through the respiratory gas path 27, and the switching mechanism 46 opens the connection 41 in order to switch a control pressure to the patient valve 39
  of a two-hose system, the gas control device (10) activates the switching mechanism 13a, 47 to block a respiratory gas flow through the respiratory gas path 27, and the switching mechanism 46 blocks the connection 41.

The gas control device 10 is embodied pneumatically and/or electronically and, in accordance with a user specification, via a user interface (not shown) or automatically, if the hose systems because of technical identifiers are identified by an identification system of the ventilator, presets the ventilator for use of the alternative hose systems 33.

The gas control device 10 comprises at least the nonreturn valve 28a, the bypass and the valve 13a.

The gas control device 10 comprises all of the valves and switching mechanisms and respiratory gas sources.

The respiratory gas path 27, 29 and the appliance outlet 30, and the connection 41 and the at least one switching mechanism 46, 47 are designed and configured to be alteration-free and adapter-less, and therefore a change in the hose systems 33 takes place without adapters or without tools.

The switching mechanism 47 is embodied as a valve which at least temporarily switches the rebreathing pressure of the expiration of the patient as a control pressure to the valve 13a.

The switching mechanism 46 is embodied as a closure valve which switches the control pressure originating from the respiratory gas source 25 to the pressure port 41 when the latter is connected to the patient valve 39 of the single-hose system.

The pressure sensor 40 is switched to inactive when a leakage system 33b is used, but can also remain active if the hose system has a pressure-measuring point.

The flow sensor 32c is switched to inactive or is not used when a leakage system 33b is used.

The flow system 32c is switched to inactive when a single-hose system 33a is used.

The control pressure for the valve 13a, 39 and 43 can be at least partially or temporarily extracted from the patients rebreathing.

FIGS. 13 to 15 show the following:

The gas control device 10 is designed and configured for use:
- of a leakage system 33b to activate the switching mechanism 13a, 47 to open the respiratory gas path 27 (bypass) for the respiratory gas flow
- of a valve system 33a with a patient valve 39 to activate the switching mechanism 13a, 47 to block a respiratory gas flow through the respiratory gas path 27, and activates the switching mechanism 46 to open the connection 41 in order to switch a control pressure to the patient valve 39
- of a two-hose system to activate the switching mechanism 13a, 47 to block a respiratory gas flow through the respiratory gas path 27 and to activate the switching mechanism 46 to block the connection 41.

The gas control device 10 is embodied pneumatically and/or electronically and, in accordance with a user specification, via a user interface, or automatically, if the hose systems because of technical identifiers are identified by an identification system of the ventilator, presets the ventilator for use of the alternative hose systems 33.

The gas control device 10 comprises, for example, at least the nonreturn valve 28a, the bypass and the valve 13a. The gas control device 10 comprises all of the valves and switching mechanisms and respiratory gas sources.

The gas control device 10 comprises, for example, appliance outlet 30, 38, connection 40, 41 and at least one switching mechanism 46, 47 and is designed and configured to be alteration-free and adapter-less such that a change of the hose systems 33 is possible without adapters or without tools.

In particular, the appliance inlet and the appliance outlet remain alteration-free on the ventilator. For the use of the different hose systems, adapters for the appliance inlet and the appliance outlet are not necessary in the event of a change of said hose systems. In particular, appliance inlet or appliance outlet or the ports or connections do not have to be closed with stoppers or caps.

LIST OF REFERENCE NUMERALS

10 Gas control device
11 First gas duct
12 Second gas duct
13a, b, c, d Switching mechanism
14 Opening
15 Sealing membrane
16 Closure cap of the opening
17 Weight
18 Extensions of the closure cap
19 Nonreturn valve
20 Connection
21 Bypass duct
22 Edge of the opening/elevation
23 Boundary of the sealing membrane
24 Edge of the bypass channel
25 Blower
26 Ventilator
27 Bypass
28a, b Nonreturn valve
29a, b First respiratory gas path, inspiratory respiratory gas path
29c, d Second respiratory gas path, expiratory respiratory gas path
30a, b Appliance outlet
31a, b Appliance inlet
32a, b, c, d Flow-measuring mechanism
33 Hose system
33a Single-hose system with patient valve 39
33b Single-hose system with leakage system
33c Two-hose system
34 First branch of two-hose system
35 Second branch of two-hose system
36 Patient interface
37a, b, c Expiratory appliance outlet
38 Expiratory appliance inlet
39 Patient valve
40 Pressure sensor
41 Patent valve connection
42 Temperature sensor
43 Internal patient valve
44 Expiratory block
45 Inspiratory block
45a Pressure side
45b Suction side
46 Valve

What is claimed is:

1. A ventilator for use with alternative hose systems, wherein the ventilator comprises at least one respiratory gas source, at least one respiratory gas path, at least one appliance outlet, an appliance inlet, and a gas control device for presetting the ventilator for use of the alternative hose systems by switching at least one switching mechanism, the gas control device being configured for use with a hose system, which is a leakage system, for opening the respiratory gas path (bypass) for a respiratory gas flow, and is further configured for use with a two-hose system to block the respiratory gas path and to block a connection.

2. The ventilator of claim 1, wherein the gas control device is further configured to activate a first and a second switching mechanism to open the respiratory gas path (bypass) for a respiratory gas flow and to activate a third switching mechanism to close a connection.

3. The ventilator of claim 1, wherein the gas control device is further configured not to conduct a control pressure to a patient valve and not to activate/use a flow sensor.

4. The ventilator of claim 1, wherein the gas control device is further configured for use with a hose system, which is a valve system with a patient valve, to block the respiratory gas path and to open a connection in order to switch a control pressure to the patient valve.

5. The ventilator of claim 4, wherein the gas control device is further configured not to conduct a control pressure to the patient valve and not to activate/use a flow sensor.

6. The ventilator of claim 1, wherein the gas control device is further configured for use with a valve system, the valve system configured for use with a patient valve to activate a first and a second switching mechanism to block a respiratory gas flow through the respiratory gas path and to activate a third switching mechanism to open a connection in order to switch a control pressure to the patient valve.

7. The ventilator of claim 1, wherein the gas control device is embodied pneumatically and/or electronically and, in accordance with a user specification, via a user interface, or automatically, if the hose systems because of technical identifiers are identified by an identification system of the ventilator, presets the ventilator for use of the alternative hose systems.

8. The ventilator of claim 1, wherein the gas control device comprises at least a nonreturn valve, the bypass and a valve.

9. The ventilator of claim 1, wherein the respiratory gas path, an appliance outlet, a connection and the at least one switching mechanism are configured to be alteration-free and adapter-less such that a change of the alternative hose systems is possible without adapters or without tools.

10. The ventilator of claim 1, wherein a switching mechanism is embodied as a first valve which at least temporarily switches a non-return respiratory pressure of an expiration of a patient as a control pressure to a second valve.

11. The ventilator of claim 1, wherein a switching mechanism is embodied as a closure valve which switches a control pressure originating from the respiratory gas source to a pressure port when the latter is connected to a patient valve of a single-hose system.

12. The ventilator of claim 1, wherein a pressure sensor is switched to inactive when the leakage system is used, but can also remain active if the hose system has a pressure-measuring point.

13. The ventilator of claim 1, wherein a flow sensor is switched to inactive or is not used when the leakage system is used.

14. The ventilator of claim 1, wherein a flow sensor is switched to inactive when a single-hose system is used.

15. The ventilator of claim 1, wherein the gas control device is designed to ensure a conducting of gas in a ventilator with an operatively connected leakage hose system and with an operatively connected valve hose system, the gas control device being configured to be alteration-free in the ventilator in the event of a change between leakage hose system and valve hose system.

16. The ventilator of claim 1, wherein the ventilator comprises a respiratory gas path which extends between an appliance inlet and an appliance outlet, the respiratory gas path comprising a respiratory gas drive and the gas control device with a nonreturn valve, a bypass and the switching mechanism, wherein the respiratory gas drive conducts an inspiratory respiratory gas flow from the appliance inlet through the nonreturn valve to the appliance outlet, and wherein the nonreturn valve is designed and arranged to prevent a respiratory gas flow in a direction of the appliance inlet (in a blocking direction of the nonreturn valve), and the bypass is configured and arranged to permit a respiratory gas flow for bypassing the nonreturn valve, and the switching mechanism is configured and arranged to at least temporarily permit or to interrupt a respiratory gas flow through the bypass for bypassing the nonreturn valve.

17. The ventilator of claim 1, wherein the switching mechanism is arranged in the bypass, and the bypass branches off from the respiratory gas path, upstream of a nonreturn valve, and opens again downstream of the nonreturn valve into the respiratory gas path or into an appliance inlet.

18. The ventilator of claim 1, wherein a respiratory gas drive is arranged between an appliance inlet and a nonreturn valve or between a nonreturn valve and an appliance outlet.

19. The ventilator of claim 1, wherein a switching mechanism is arranged in the bypass, and the bypass branches off between a respiratory gas drive and a nonreturn valve and opens again between the nonreturn valve and an appliance outlet into the respiratory gas path, and wherein the respiratory gas drive is arranged between an appliance inlet and the nonreturn valve, and, via a switching mechanism arranged in the bypass, respiratory gas can be returned in a direction of the appliance inlet, as a result of which the nonreturn valve is bypassed.

20. The ventilator of claim 1, wherein the switching mechanism is arranged in the bypass, and the bypass branches off between an appliance inlet and a nonreturn valve and opens again between the nonreturn valve and a respiratory gas drive into the respiratory gas path, wherein the respiratory gas drive is arranged between the nonreturn valve and an appliance outlet and, via the switching mechanism arranged in the bypass, respiratory gas can be returned in a direction of the appliance inlet after it has passed through the respiratory gas drive.

21. The ventilator of claim 1, wherein a gas-measuring mechanism is arranged between the bypass and an appliance outlet and is configured to detect a flow or a volume or a pressure of the respiratory gas in the respiratory gas path, and the switching mechanism is designed and configured to set a PEEP (positive end-expiratory pressure) in a range of 0-20 hPa.

22. The ventilator of claim 1, wherein the ventilator comprises an expiratory respiratory gas path which extends from an expiratory appliance inlet to an expiratory appliance outlet and comprises a switching mechanism and a gas-measuring mechanism, the gas-measuring mechanism being arranged between the expiratory appliance outlet and the switching mechanism.

23. The ventilator of claim 1, wherein a hose system is mounted on an appliance outlet, the hose system comprising a first branch and a second branch, the first branch leading from the appliance outlet to a patient interface, and the second branch leading from the patient interface to an expiratory appliance inlet, and wherein inspiratory respiratory gas is conducted from the inspiratory respiratory gas path to the patient interface via the first branch, and expiratory respiratory gas is conducted from the patient interface to the expiratory respiratory gas path via the second branch.

24. The ventilator of claim 1, wherein in the event of a blockage/disturbance of a first expiratory respiratory gas path, the expiratory respiratory gas can be conducted away into a second inspiratory respiratory gas path and via the open bypass into the surroundings by control of a switching mechanism.

25. The ventilator of claim 1, wherein the ventilator comprises a first inspiratory respiratory gas path and a second inspiratory respiratory gas path, as well as a first expiratory respiratory gas path and a separate second expiratory respiratory gas path.

26. A ventilator for use with alternative hose systems, wherein the ventilator comprises at least one respiratory gas source, at least one respiratory gas path, at least one appliance outlet, an appliance inlet, and a gas control device for presetting the ventilator for use of the alternative hose systems by switching at least one switching mechanism, the gas control device being configured for use with a hose system, which is a leakage system, for opening the respiratory gas path (bypass) for a respiratory gas flow, and is further configured to activate a first and a second switching mechanism to block a respiratory gas flow through the respiratory gas path and to activate a third switching mechanism to block a connection.

27. The ventilator of claim 26, wherein the ventilator comprises a respiratory gas path which extends between an appliance inlet and an appliance outlet, the respiratory gas path comprising a respiratory gas drive and the gas control device with a nonreturn valve, a bypass and the switching mechanism, wherein the respiratory gas drive conducts an inspiratory respiratory gas flow from the appliance inlet through the nonreturn valve to the appliance outlet, and wherein the nonreturn valve is designed and arranged to prevent a respiratory gas flow in a direction of the appliance inlet (in a blocking direction of the nonreturn valve), and the bypass is configured and arranged to permit a respiratory gas flow for bypassing the nonreturn valve, and the switching mechanism is configured and arranged to at least temporarily permit or to interrupt a respiratory gas flow through the bypass for bypassing the nonreturn valve.

28. A ventilator for use with alternative hose systems, wherein the ventilator comprises at least one respiratory gas source, at least one respiratory gas path, at least one appliance outlet, an appliance inlet, and a gas control device for presetting the ventilator for use of the alternative hose systems by switching at least one switching mechanism, the gas control device being configured for use with

- a leakage system to activate a first and a second switching mechanism to open the respiratory gas path (bypass) for a respiratory gas flow;
- a valve system with a patient valve to activate a first and a second switching mechanism to block a respiratory gas flow through the respiratory gas path, and to activate a third switching mechanism to open a connection in order to switch a control pressure to the patient valve; or
- a two-hose system to activate a first and a second switching mechanism to block a respiratory gas flow through the respiratory gas path and to activate a third switching mechanism to block a connection.

29. The ventilator of claim 28, wherein the ventilator comprises a respiratory gas path which extends between an appliance inlet and an appliance outlet, the respiratory gas path comprising a respiratory gas drive and the gas control device with a nonreturn valve, a bypass and the switching mechanism, wherein the respiratory gas drive conducts an inspiratory respiratory gas flow from the appliance inlet through the nonreturn valve to the appliance outlet, and wherein the nonreturn valve is designed and arranged to prevent a respiratory gas flow in a direction of the appliance inlet (in a blocking direction of the nonreturn valve), and the bypass is configured and arranged to permit a respiratory gas flow for bypassing the nonreturn valve, and the switching mechanism is configured and arranged to at least temporarily permit or to interrupt a respiratory gas flow through the bypass for bypassing the nonreturn valve.

\* \* \* \* \*